United States Patent [19]
Wright et al.

[11] Patent Number: 5,354,000
[45] Date of Patent: Oct. 11, 1994

[54] SHARPS DISPOSAL SYSTEM
[75] Inventors: Glenn A. Wright, 22101 Rockport La., Huntington Beach, Calif. 92648; Philip F. Fritz, Ontario, Calif.; Tuan Q. Nguyen, Anaheim, Calif.
[73] Assignee: Glenn Albert Wright, Huntington Beach, Calif.
[21] Appl. No.: 143,491
[22] Filed: Oct. 25, 1993

Related U.S. Application Data
[63] Continuation of Ser. No. 876,314, May 5, 1992, abandoned.
[51] Int. Cl.⁵ ............................................. B02C 23/36
[52] U.S. Cl. .................... 241/33; 241/46.017; 241/100; 241/606
[58] Field of Search ............ 241/606, 33, 242, 46.017, 241/46.08, 99, 16, 100

[56] References Cited

U.S. PATENT DOCUMENTS

| | | |
|---|---|---|
| 2,641,165 | 6/1953 | Wandel . |
| 3,194,505 | 9/1962 | Spackman ..................... 241/46.08 |
| 3,386,668 | 6/1968 | Shepherd .................... 241/46.017 |
| 3,436,027 | 4/1969 | Sherman, Jr. . |
| 3,455,518 | 7/1969 | Chambers, Sr. . |
| 3,620,460 | 11/1971 | Hunker . |
| 3,982,703 | 9/1978 | Meyers . |
| 4,032,446 | 6/1977 | Miller, Jr. . |
| 4,037,795 | 7/1977 | Fyfe . |
| 4,185,973 | 1/1980 | Tester . |
| 4,531,437 | 7/1985 | Szablak et al. . |
| 4,619,409 | 10/1986 | Harper et al. . |
| 4,884,756 | 12/1989 | Pearson . |
| 4,889,290 | 12/1989 | Koffsky et al. . |
| 4,971,261 | 11/1990 | Solomons . |
| 4,984,748 | 1/1991 | Kimura . |
| 5,007,590 | 4/1991 | Taylor . |
| 5,025,994 | 6/1991 | Maitlen et al. . |
| 5,035,367 | 7/1991 | Nojima ............................. 241/37.5 |
| 5,046,669 | 9/1991 | Wallace ................................ 241/23 |
| 5,054,696 | 10/1991 | Mennel ................................ 241/34 |

FOREIGN PATENT DOCUMENTS

| | | |
|---|---|---|
| 67862 | of 0000 | China . |
| 85037 | of 0000 | China . |
| 135339 | 12/1978 | China . |
| 54823 | 6/1982 | European Pat. Off. . |
| 122399 | 6/1985 | Japan . |

OTHER PUBLICATIONS

"Microwave Treatment of Infectious Waste", *Tech Application*, No. 1 (1991) (published by EPRI Industrial Program Environmental & Energy Management).
"Cutler Hammer Programmable Controllers", *Fisher Scientific Catalog*, p. 189 (Oct. 1, 1988).
"Omega SDS", American Delphi mailer (1990) (month unknown).
"Chemical Pumps from Little Giant ®", Little Giant Brochure, Jan. 1990.
"30 Beds/One System" advertisement (date unknown).
"Destruction and Decontamination of Infectious Waste," Medical Safetec advertisement (date unknown).
"In Room Sharps Disposal" advertisement (date unknown).
"Isolyser Medical Waste Treatment Systems", Isolyser Company, Inc. Brochure (date unknown).
"Horizontal Drop Sharps Disposal Containers", Sage Products, Inc. advertisement, 1990 (month unknown).
"How to Use the Large Volume In-Room Wall Enclosure System" product description (date unknown).

*Primary Examiner*—Douglas D. Watts
*Attorney, Agent, or Firm*—Knobbe, Martens, Olson & Bear

[57] ABSTRACT

A sharps disposal apparatus is provided for reducing contaminated medical sharps into unrecognizable, ordinary waste. The disposal apparatus comprises a disposal unit including a disposer, disposable waste receptacle, and sterilant recycling system. During the destruction and sterilization operation, the sterilant recycling system introduces sterilant into the disposer to sterilize the contaminated medical sharps while the disposer is grinding the sharps into small fragments. Once the medical waste is reduced to small fragments and is sterilized, the reduced waste is deposited in the disposable waste receptacle. Excess disinfectant flows through the waste receptacle and is recovered by a reservoir to be recycled. After the waste receptacle is full, the waste receptacle is easily removed from disposal unit, without the reduced medical waste coming into contact with human hands, and is disposed as ordinary waste.

16 Claims, 11 Drawing Sheets

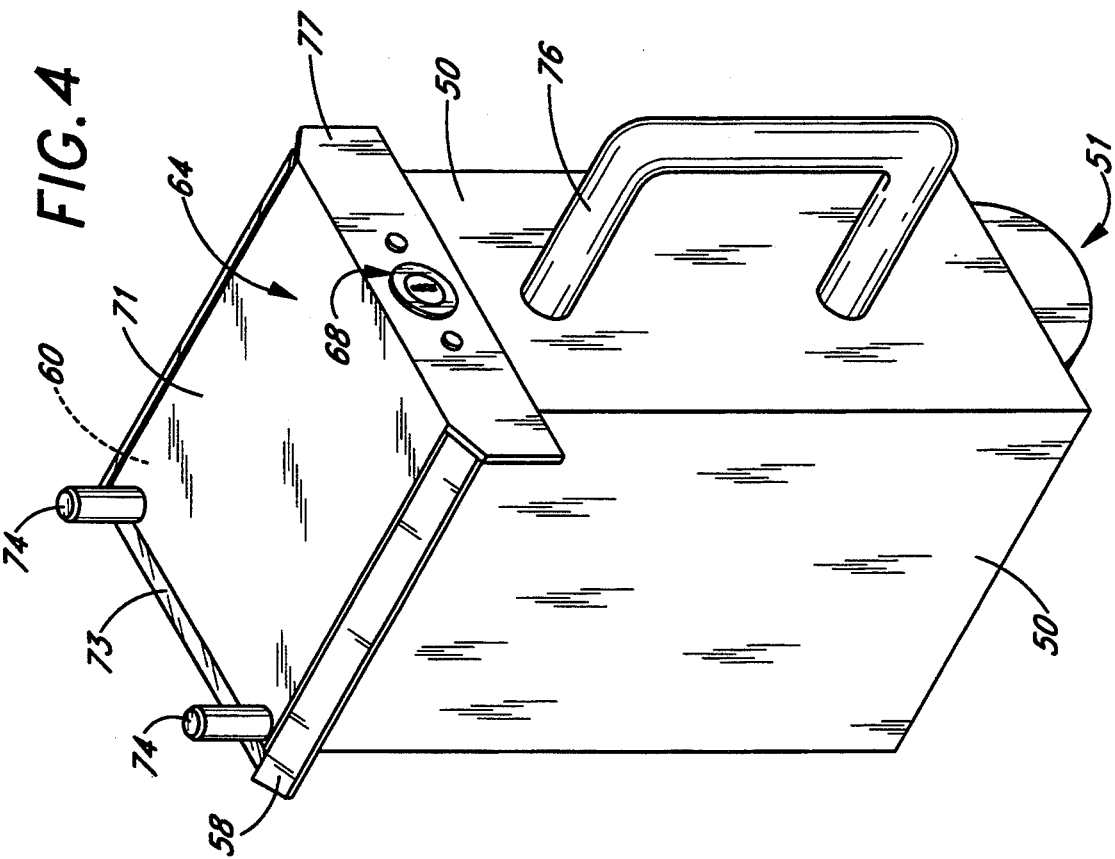
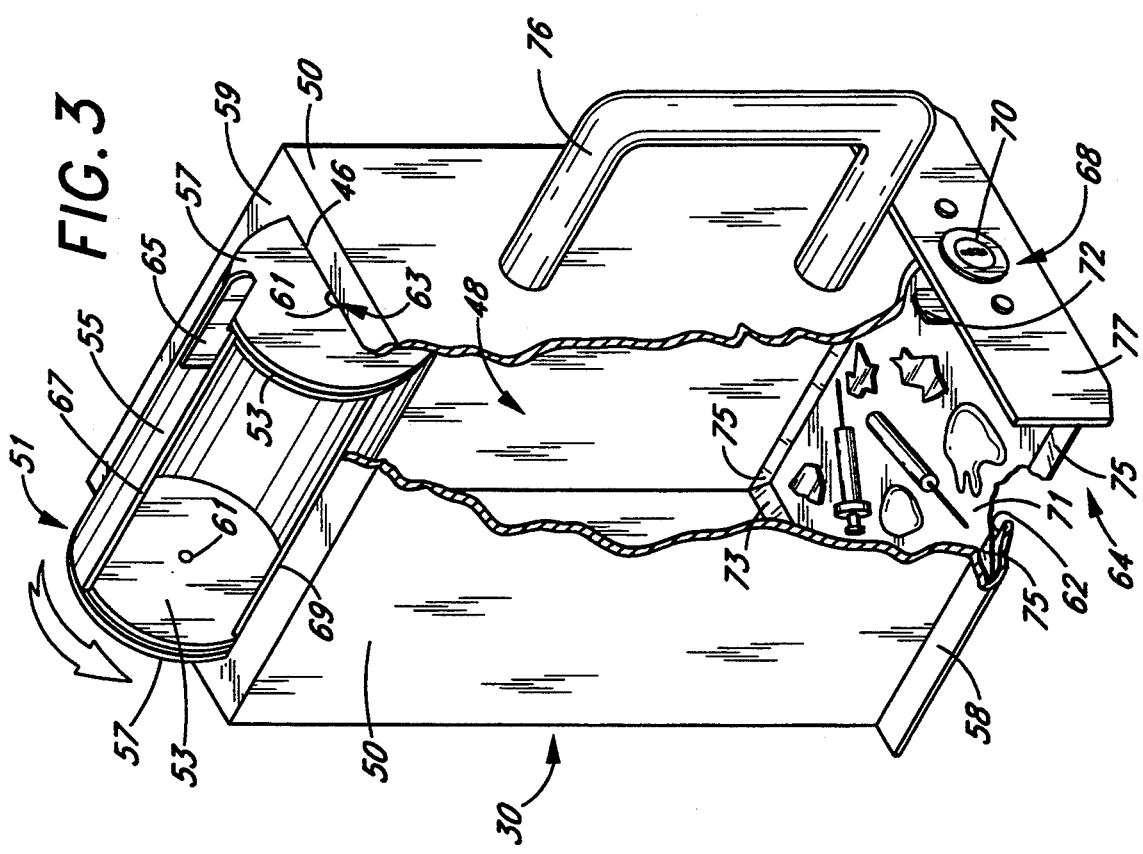

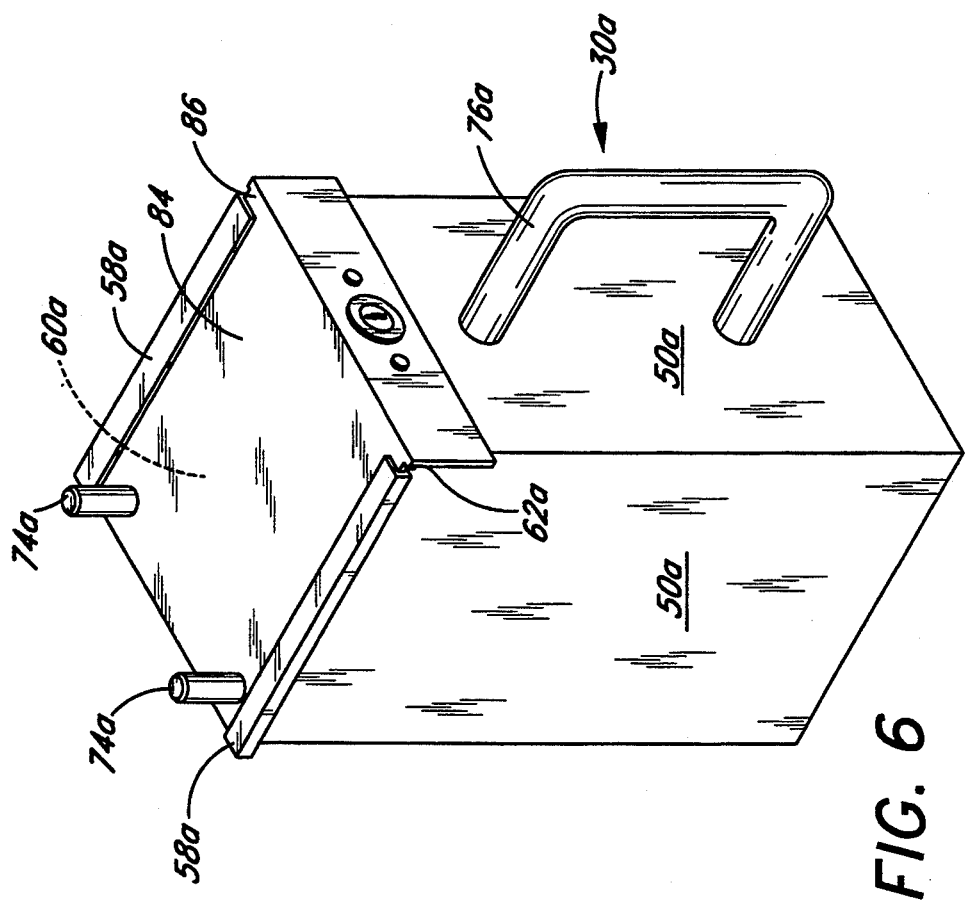
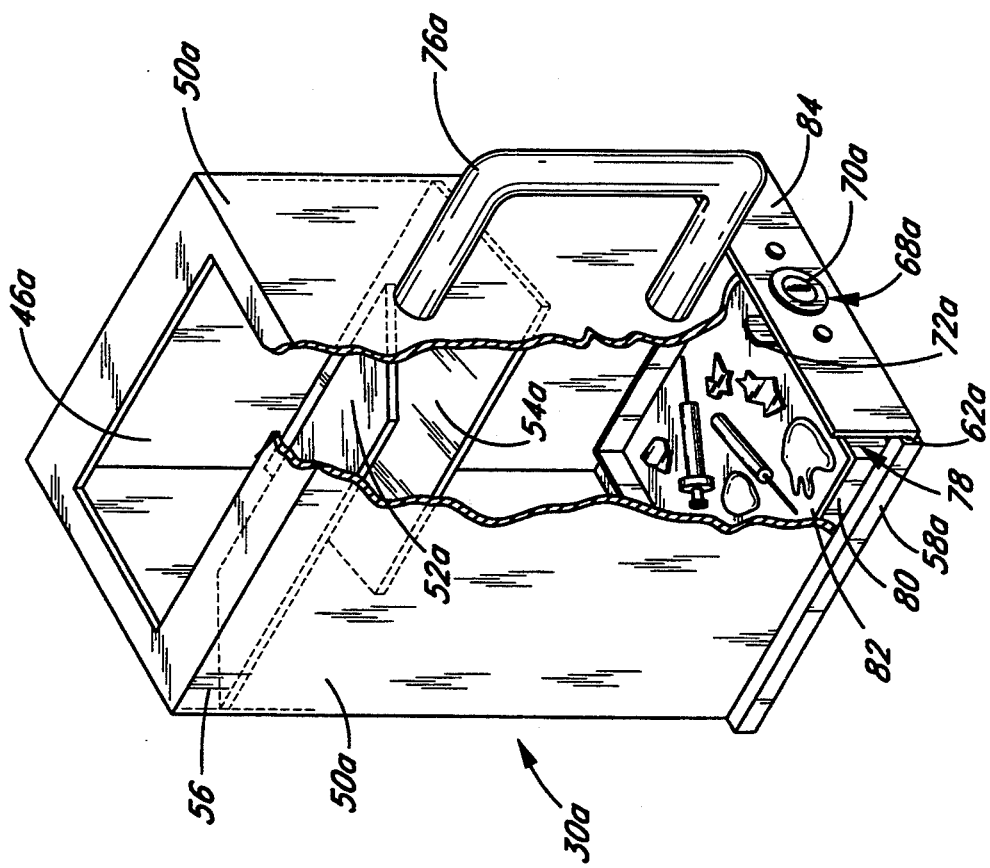

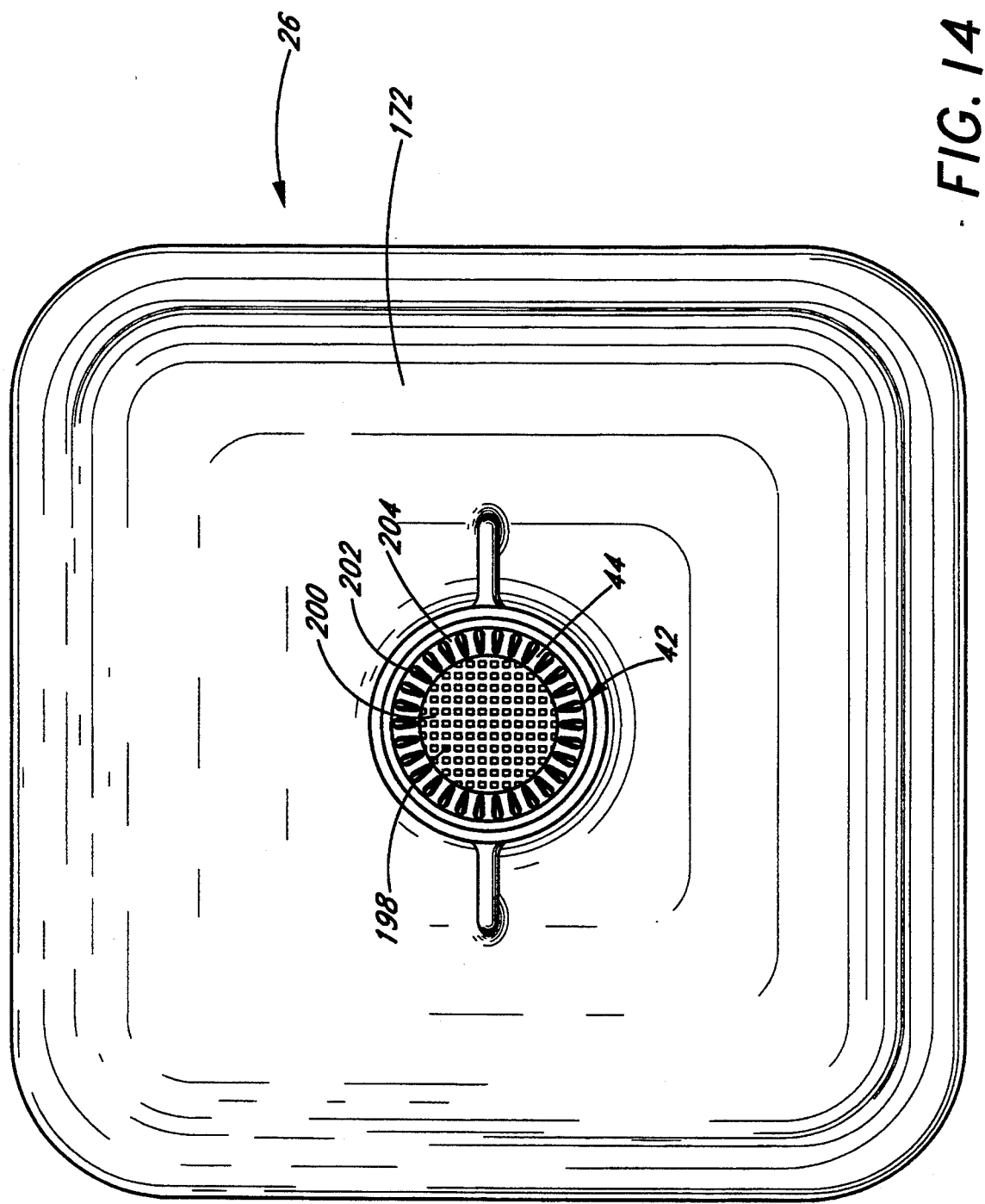

SHARPS DISPOSAL SYSTEM

This application is a continuation of application Ser. No. 07/876,314, filed May 5, 1992.

BACKGROUND OF THE INVENTION

1. Field of the Invention

The present invention relates to a medical waste disposal system and, in particular, to a disposal system used to destroy and decontaminate infectious medical sharps. The present invention also relates to a method of managing infectious or hazardous medical waste.

2. Description of Related Art

The problems attendant to the destruction and decontamination of medical waste, such as needles, syringes, vials, plastic blood bags, plastic tubes, etc. are formidable. Medical waste presents problems not only because sharps such as needles and syringes are hazardous and difficult to destroy, but also because the waste may be contaminated with viral and bacterial pathogens.

The prevalent practice in the medical community for the disposal of medical waste is to throw the waste into specially sealed containers labeled as hazardous waste. A disposal service periodically collects the containers and dumps the containers into huge disposal machines. The disposal machines incinerate or pulverize and sterilize the waste for deposit in a landfill. Unscrupulous disposal services, however, have previously illegally dumped unprocessed medical waste into the ocean or landfills, contaminating the environment.

In an effort to curtail illegal dumping of medical waste, the United States Congress enacted the Medical Waste Tracking Act, which became effective in 1989. The Medical Waste Tracking Act requires medical waste generators (i.e., persons or entities producing medical waste) to segregate waste at their point of origin and package sharps (e.g., syringes, needles, glass vials, etc.) into rigid, puncture-resistant, leak-resistant containers in order to transport the materials off-site. Generators must also label the untreated waste as medical waste, and most generators must track (i.e., maintain a written record of) the disposal process of the waste from the point of origin to the final disposal site.

Because of the onerous tracking procedures imposed by the Medical Waste Tracking Act and because of the considerable expense associated with disposal of medical waste, especially sharps, various devices for on-site destruction of used sharps have been developed. These devices typically grind or otherwise reduce medical sharps into small pieces and direct the fragments into a receptacle for disposal. For examples, see U.S. Pat. Nos. 4,531,437, issued to Szablak, et al.; 4,889,290, issued to Koffsky, et al.; 4,971,261, issued to Solomons; 4,984,748, issued to Kimura; and 5,025,994, issued to Maitlen, et al.

In addition, disposal devices have been developed which purport to decontaminate as well as destroy the medical waste. For examples, see U.S. Pat. Nos. 4,619,409, issued to Harper, et al.; 4,884,756, issued to Pearson; 4,889,290, issued to Koffsky, et al.; 4,971,261, issued to Solomons; and 5,025,994, issued to Maitlen, et al. Medical waste which has been destroyed and decontaminated on-site can subsequently be disposed as ordinary refuse, thereby reducing the costs associated with off site disposal services. The prior disposal systems, however, suffer from several drawbacks.

Many prior disposal systems waste decontaminant, often using more decontaminant than is required to adequately disinfect the medical waste. For instance, the disposal devices disclosed in the Koffsky, et al., and Solomons patents direct both the processed waste and the decontaminant into disposable receptacles. The excess decontaminant fluid discarded with the medical waste increases the expense of medical waste disposal and may pollute ground water when disposed in landfills.

Further, many prior disposal systems do not adequately safeguard the system operators, requiring at least some human contact after introducing the medical waste. For instance, the disposal systems disclosed in the Kimura, Harper et al. and Pearson patents use permanent waste bins which must be periodically emptied. The Szablak, et al. and Koffsky, et al. patents disclose devices which require the handlers of the medical waste to deposit the waste in the disposer unit. Such disposal systems are particularly unsuitable for institutional applications where relatively unskilled workers are employed to operate the disposal system. Consequently, prior disposal systems present potentially liability issues and may not adequately safeguard the operators from the infectious medical waste being processed.

Thus, a need exists for a waste disposal apparatus and management system which efficiently, ergonomically and cost-effectively reduces contaminated medical sharps to unrecognizable, ordinary waste for disposal.

SUMMARY OF THE INVENTION

In accordance with one aspect of the invention, there is provided an apparatus for rendering potentially contaminated sharps into a form suitable for disposal as ordinary waste. Sharps are initially deposited into a remote container known in the art as a wall-safe. The sharps are then fed directly from the wall-safe into a disposer. Liquid sterilant is directed into the disposer and is thoroughly mixed with the sharps to disinfect them as the sharps are ground into a predetermined particle size.

After the sharps have been ground and disinfected, the particulate waste falls into a receptacle. The receptacle is a disposable sealable receptacle which is removed from the apparatus when full and subsequently sealed and disposed as ordinary waste. The receptacle has an effluent port near the bottom thereof for drainage of excess sterilant. Excess sterilant which does not adhere to the ground sharps is recovered by a recirculation system which recycles the sterilant to the disposer for reuse. Preferably, the receptacle includes a filter disposed over the effluent port to prevent escape of processed waste.

In a preferred embodiment, the recirculation system comprises a reservoir, typically positioned below the effluent port of the waste receptacle, to recover excess sterilant. The reservoir is preferably in selective communication with a chemical supply source and with a water supply source. A microprocessor in communication with a detector is used to monitor the concentration of a chemical agent in the aqueous sterilant and to automatically introduce fresh chemical agent from the chemical supply source into the sterilant based upon preselected concentration criteria.

In another preferred embodiment, the disposer comprises a grinding chamber and a shear ring. The shear ring defines an interior annular surface and supports an array of spaced teeth which project inwardly towards the center of the shear ring. Each tooth extends from the shear ring interior surface at an angle from and in a plane parallel to a central vertical axis of the disposer. Each tooth also has a generally flat bottom surface defining a shearing edge. A plurality of the teeth have top portions extending above the tops of the other teeth and at a greater angle relative to the central axis to define inverted, generally L-shaped teeth in the array of teeth.

The preferred disposer additionally includes a disk rotatable about the central axis. The disk carries a cutter element which forms a shearing surface and is positioned to engage the shearing surfaces defined by the array of teeth. The shearing surface of the cutter element cooperates with the teeth to trap, rip, cut, shear and slice the medical waste into harmless fragments as the disk rotates.

In accordance with another aspect of the invention, there is provided a disposal system for processing and sterilizing medical waste. The disposal system comprises a container having an exit opening and a disposal unit having an opening for receiving materials from the container by way of the exit opening. The disposal system additionally includes an engagement structure on the disposal unit for engaging the container and placing the exit opening in communication with the disposal unit opening.

In a preferred embodiment, the container includes an inlet opening to deposit medical waste into the container, a baffle positioned to substantially prevent deposited medical waste from spilling through the inlet opening, and a door which normally closes the exit opening. The container also includes a locking mechanism coupled to the door to prevent unauthorized persons from removing the door from the container.

The preferred engagement structure comprises a pair of rails which engages the container. The door and the engagement structure also have at least one interengaging structure which holds the door stationary while the container is slid between the rails. The rails are positioned proximate to the opening of the disposal unit such that as the container is slid with the door remaining substantially stationary, the exit opening of the container is placed into communication with the opening of the disposal unit. The engagement structure automatically opens the door of the container to place the exit opening in communication with the disposal unit opening. The disposal unit additionally comprises a door normally closing the opening of the disposal unit which automatically opens as the engagement structure engages the container.

In accordance with a preferred method of reducing contaminated medical sharps to unrecognizable, ordinary waste, contaminated medical sharps are deposited into a disposer and a sterilant is sprayed into the disposer to generally sterilize the medical sharps. The medical sharps are ground into small fragments to form a slurry of processed waste and excess sterilant which is then deposited into a disposable waste receptacle having at least an influent port and an effluent port.

Excess sterilant is filtered through a filter placed in the receptacle and recovered by a recirculation system which recycles the recovered sterilant back into the disposer. The waste receptacle is thereafter sealed and removed from the disposer. Preferably, sealing is accomplished by placing a snap fit or threaded cap over each of the influent port and effluent port. The sealed receptacle is then discarded.

A further aspect of the present invention involves a method of disposing contaminated medical waste, such as sharps, accumulated in a medical facility, while minimizing human contact with the medical waste. The method includes the steps of placing at least one medical waste depository in the medical facility and thereafter collecting the depository after medical waste has been placed therein. The depository is engaged with a disposal unit and the medical waste is emptied into the disposal unit. The medical waste is then processed into small fragments, sterilized, and deposited into a deposable waste receptacle for disposal.

BRIEF DESCRIPTION OF THE DRAWINGS

These and other features of the invention will now be described with reference to drawings of a preferred embodiment which is intended to illustrate and not to limit the invention, and in which:

FIG. 3 is a top perspective, partial cut-away view of a wall-safe of the waste disposal system of FIG. 1;

FIG. 4 is a bottom perspective view of the wall-safe of FIG. 3;

FIG. 5 is a top perspective, partial cut-away view of a second embodiment of a wall-safe in accordance with the present invention;

FIG. 6 is a bottom perspective view of the wall-safe of FIG. 5;

FIG. 14 is a bottom plan view of the waste receptacle of FIG. 12.

DETAILED DESCRIPTION OF PREFERRED EMBODIMENTS

Figure 1:
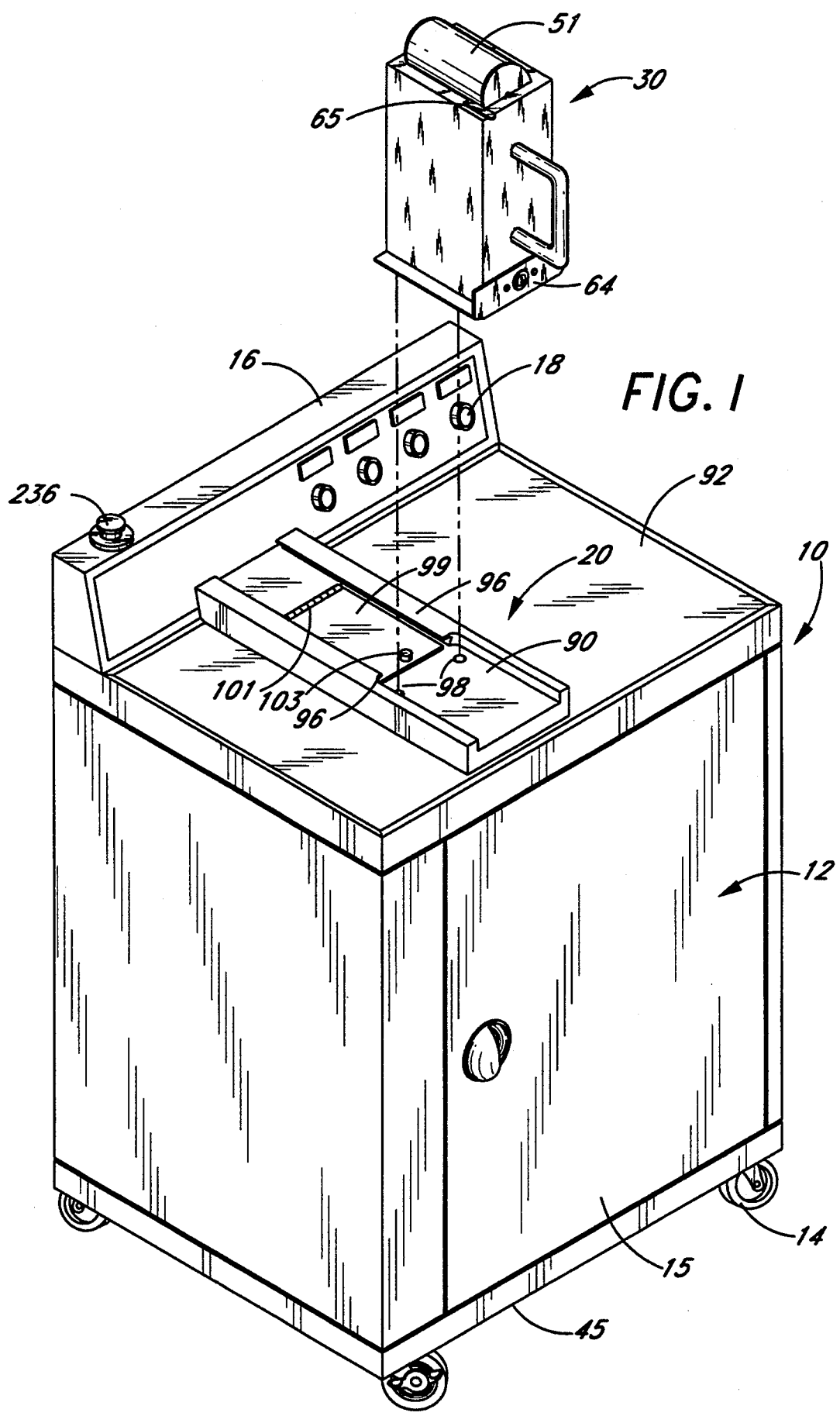
FIG. 1 is a perspective view of a waste disposal system in accordance with the present invention.

FIG. 1 illustrates a medical waste disposal unit 10 in accordance with a preferred embodiment of the present invention. The disposal unit 10 processes contaminated medical waste, including sharps, into unrecognizable, ordinary waste. As used herein, "sharps" means sharp medical waste items, such as, for example, hypodermic syringes or needles, intravenous needles, Petri dishes, vials and the like.

A compact, rugged stainless steel cabinet 12, mounted on locking caster wheels 14, houses the components of the disposal unit 10. The cabinet 12 is preferably sized to unobtrusively fit in a standard size room of a medical facility for on-site disposal of medical waste. More preferably, the cabinet 12 in accordance with one embodiment has the following dimensions: 36.0 inches (91.4 centimeters (cm)) by 25.0 inches (63.5 cm) by 41 inches (104.1 cm). As will be readily appreciated by one of skill in the art, disposal systems incorporating the present invention can be manufactured in any of a wide variety of sizes and configurations in addition to those disclosed herein.

The cabinet 12 includes a front door 15 which provides access to the contents of cabinet 12. The cabinet 12 also preferably has a removable back panel (not shown) for access into the rear of the disposal unit 10.

The cabinet 12 includes a control and display panel 16 which supports a plurality of indicator lights 18, which alert the operator to the disposal cycle's status, including an indicator to signal time to remove a receptacle filled with decontaminated waste. The specific operation of the indicator lights 18 will be discussed below.

Figure 2:
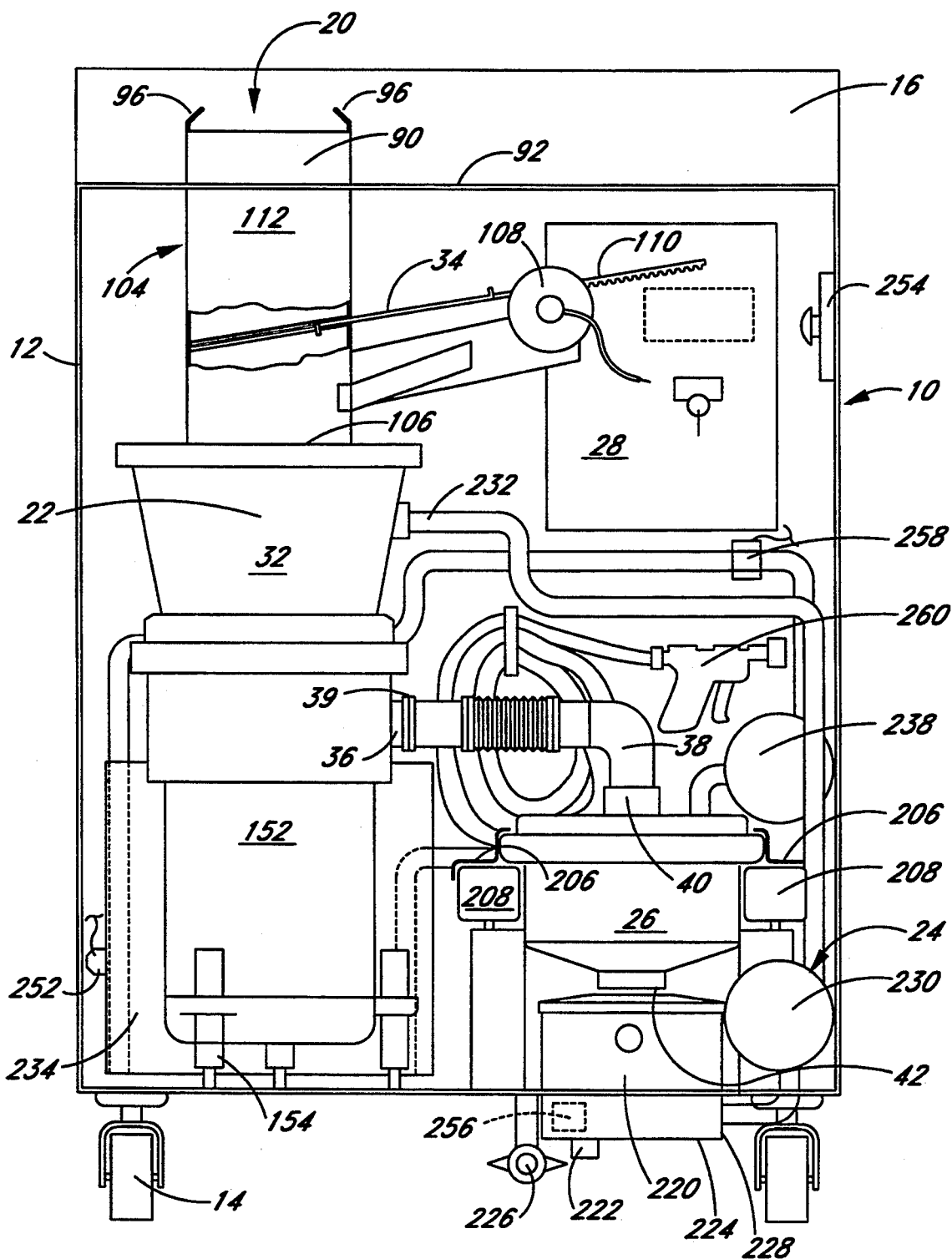
FIG. 2 is a schematic elevational view of the internal components of the waste disposal system of FIG. 1.

FIG. 2 schematically illustrates the components of the disposal unit 10. The disposal unit 10 principally comprises a hopper mechanism 20 connected to a disposer 22, a sterilant recirculation system 24 defining a circular fluidic path between a disposable waste receptacle 26 and the disposer 22, and a program logic computer 28 which controls the functioning of the disposer unit 10.

Referring to FIGS. 1 and 2, the hopper mechanism 20 interacts with a reusable wall-safe or "mailbox" 30 to receive contaminated waste collected in the wall-safe 30 from a remote area of the medical facility. As used herein, "medical facility" designates a hospital, a physician or veterinarian office, a medical clinic or a like treatment facility which may generate waste of the type which is desirably treated by destruction and sterilization.

The hopper mechanism 20 communicates with the disposer 22 in a manner discussed in detail infra. Medical waste falls into a grinding chamber 32 of the disposer 22 when a retractable gate 34 of the hopper mechanism 20 opens. The disposer 22 grinds the medical waste into small unrecognizable fragments of metal, plastic, glass, etc., thus rendering the medical waste harmless. The disposer preferably grinds the waste into fragments having a size less than 1.0 inch (2.54 cm), more preferably less than 0.25 inch (0.64 cm), and most preferably less than 0.125 inch (0.32

During the grinding process, the recirculation system 24 sprays sterilant into the grinding chamber 32 of the disposer 22 to substantially sterilize the medical waste in the grinding chamber 32. The ground medical waste and sterilant form a slurry which flows from a discharge port 36 of the disposer 22, through a discharge conduit 38 and into the disposable waste receptacle 26. A gasket 39 seals the interconnection between discharge port 36 and the discharge conduit 38.

The disposable waste receptacle 26 receives the slurry of processed medical waste and sterilant through at least one influent port 40. The medical waste deposits in a containing cavity defined by the waste receptacle 26. The waste receptacle 26 also includes at least one effluent port 42 through which excess sterilant flows from the waste receptacle 26. That is, sterilant not adhering to the processed waste flows through the processed waste and out the effluent port 42. The waste receptacle 26 further includes a filter 44 disposed across the flow path through the effluent port 42 to substantially prevent the processed waste from escaping through the effluent port 42.

The recirculation system 24 recovers the excess sterilant flowing through the effluent port 42 and recycles the sterilant to the disposer 22 for further sterilization of additional medical waste placed in the disposer 22.

The program logic computer 28 preferably monitors each function during the destruction and decontamination process and indicates to the operator when the waste receptacle 26 has been filled. Thereafter, the waste receptacle 26, filled with ground, unrecognizable, medical waste, is disposed as ordinary waste through conventional means.

The individual components of the medical waste disposal apparatus will now be discussed in detail. For the purpose of describing the invention, the terms "upper," "lower," "top," "bottom," "forward," "front," "rearward" and "rear" are used in reference to the front door 15 and a lower edge 45 of the disposer unit cabinet 12, which are illustrated in FIG. 1.

Wall-Safe

Referring to FIG. 3, the reusable wall-safe 30 has a low profile, configured to be removably mounted on a wall bracket (not shown) in a room of the medical facility where medical waste may be generated. The wall bracket and the wall-safe 30 have interconnecting structure which quickly engages to secure and support the wall-safe 30, and quickly disengages to remove the wall-safe 30. The interconnecting structure preferably engages by a snap-fit, pin/key-way connection, press-fit, tab/socket connection or like interconnection.

The wall-safe 30 has a generally rectangular box shape having an inlet aperture 46 opening into a holding chamber 48. The holding chamber 48 defined by the walls 50 of the wall-safe 30 has a volume ranging between 0.5 and 50 quarts (47.3 to 9,730 cm$^3$), more preferably ranging between 1 and 10 quarts (94.6 to 946.3 cm$^3$), and most preferably equaling about 5 quarts (473 cm$^3$). However, the dimensions and volume of the wall-safe can readily be customized to suit specific facility requirements.

The wall-safe 30 is preferably injection or rotationally molded of a durable plastic material. Preferably, the wall-safe is formed of polyvinylchloride ("PVC"), TEFLON®, polyacrylonitryl-butadienyl-styrene ("BS") or other plastics known in the medical device art. Additionally, the wall-safe is preferably formed of a translucent plastic or with at least one window therein such that medical facility personnel may determine the volume of waste in the container without directly viewing the waste.

The wall-safe 30 additionally includes a generally cylindrical dome cover 51 which precludes direct access into the holding chamber 48. The dome cover 51 comprises a pair of circular end plates 53 closing the ends of a tubular segment 55. The tubular section 55 is sectioned longitudinally such that the tubular section 55 has a circumference extending around about two-thirds of the circumference of the circular end plates 53. The dome cover 51 is coextensive with the inlet aperture 46, having a diameter equal to about the width of the inlet aperture 46 and having a length equal to about the length of the inlet aperture 46.

The wall-safe 30 includes a pair of semi--circular support plates 57 with extend perpendicularly from a top plate 59 of the wall-safe 30, generally adjacent and parallel to the short sides of the inlet aperture 46. The support plates 57 preferably have radii complementary to the radius of the dome cover 51.

A pair of rivets 61 connect the dome cover 51 to the support plates 57 and permit the dome cover 51 to rotate within the inlet aperture 46 about an axis defined between the rivets 61. The rivets 61 are preferably positioned at about a radial center point 63 of the support plates 57 such that cylindrical dome cover 51 does not significantly extend above the support plates 57. The rivets 61 are preferably positioned collinear with each other.

The dome cover 51 additionally includes an L-shaped tab 65 to manipulate the dome cover 51. As illustrated in FIG. 3, the tab 65 is preferably positioned proximate to a top edge 67 of the tubular section 55 such that the tab 65 generally extends upwardly with the interior of the dome cover 51 exposed and, as illustrated in FIG. 1, abuts the top plate 59 of the wall-safe 30 with the interior of the dome cover 51 concealed. The tab 65 thus limits rotation of the dome cover 51 when closing the dome cover 51. A lower edge 69 of the tubular section 55 abuts the lower surface of the top plate 59 to limit rotation of the dome cover 51 when opening the dome cover 51.

Referring to FIG. 4, the wall-safe 30 additionally includes a pair of brackets 58 disposed on the lower edges of the rectangular box, along the edges of a selectively sealable bottom aperture 60. Each bracket 58 has a generally U-shape or V-shape in cross-section, one segment of the bracket extending generally perpendicular to the side wall 50 and the other segment angling back toward the center of the wall-safe at about 45°, away from the bottom aperture 60. The brackets 58 thus define a pair of parallel slots 62 which receive a slidable bottom tray 64, the side edges 66 of the tray 64 sliding between the pair of parallel slots 62. In this manner, the brackets 58 support the tray 64 which closes the bottom aperture 60.

The slidably bottom tray 64 comprises a bottom 71, a front wall 73, a pair of side walls 75 and a rear wall 77. The front wall 73 and side walls 75 have a height of at least about 0.5 inches (1.3 cm) and the bottom 71 has a size generally coextensive with the bottom aperture 60. The rear wall 77 has a height sufficiently large to abut the adjacent side wall 50 of the wall-safe 30 when the tray 64 is inserted between the brackets 58. The front wall 73, sloping forwardly, preferably forms about a 15° angle with the bottom 71 and the side walls 75, sloping outwardly, preferably form about a 45° angle with the bottom 71. The rear wall 77 is preferably positioned generally perpendicular to the bottom 77. As will be readily appreciated by one of skill in the art, however, one could size the walls 73, 75, 77 of the tray 64 and position the walls 73, 75, 77 with respect to the bottom 71 at any angle so long as the tray 64 contains any fluid which may drain from the waste and so long as the waste is easily swept out of the tray 64 when the wall-safe 30 is slid over the tray 64, as discussed below.

In one preferred embodiment, a disposable, absorbent blotter (not shown) having a fluid resistant surface is positioned on top of the tray 64 with the fluid resistant surface contacting the bottom 71. The absorbent blotter completely covers the bottom 71 and desirably extends above the tray walls 73, 75. Consequently, when the wall-safe 30 is slid over the tray 64, the side wall 50 supporting the handle 76 sweeps the blotter out of the tray 64 with the waste.

The blotter preferably comprises an absorbent material, such as, for example, a sponge, and is coated on its bottom surface with a fluid resistant material, such as, for example, polyethylene. The blotter absorbs any fluids which may drain from the waste to generally keep the interior surfaces of the tray 64 free from contaminated fluids.

The tray 64 selectively seals the bottom aperture 60. The tray 64 defines an area between the upper edges of the front wall 73, side walls 75 and rear wall 77 which is coextensive with the area of the bottom aperture 60. Any fluid which drains from the waste deposited into the wall-safe 30 collects on the bottom 71 of tray 64 or in the blotter, if used. The walls 73, 75, 77 of the tray 64 contain the fluid. In addition, the labyrinth defined between the walls of the tray 64 and the brackets 58 generally prevents fluid from escaping between the tray 64 and the bottom aperture 60. It is also contemplated that a sealing member could be disposed around the interface between the tray 64 and the bottom aperture 60 to enhance the seal around the bottom aperture 60.

The bottom tray 64 preferably includes a locking mechanism 68 to prevent unauthorized persons from removing the tray 64 from the wall-safe 30. The locking mechanism 68 preferably comprises a conventional lock cylinder 70 coupled to a throw lever 72 which rotates in and out of engagement with the adjacent side wall 50 of the wall-safe 30 to lock and unlock the tray 64, respectively. The locking mechanism is preferably mounted to the rear wall 77 of the tray 64. The wall-safe 30, proximate the locking mechanism 68, includes an aperture (not shown) which receives the lock cylinder 70 and throw lever 72 when the tray 64 is inserted between the lower brackets 58.

The tray 64 also includes a pair of cylindrical pegs 74 which extend from the bottom surface of the tray 64, away from the wall-safe 30. The pegs 74 interact with the hopper mechanism 20, as discussed below.

The wall-safe 30 further includes a handle 76 to facilitate carrying the reusable wall-safe 30 between the mounting bracket (not shown) positioned in the medical facility room and the disposer unit 10 preferably located in a remote location of the medical facility.

FIGS. 5 and 6 illustrate an alternative embodiment of a wall-safe 30a for use with the present invention. Where appropriate, like numbers with an "a" suffix are used to indicated like parts of the two embodiments for ease of understanding. The wall-safe 30a has a generally rectangular box shape having an inlet aperture 46a opening into a holding chamber 48a. The holding chamber 48a defined by the walls 50a of the wall-safe 30a has a volume ranging between 0.5 and 50 quarts (47.3 to 9,730 $cm^3$), more preferably ranging between 1 and 10 quarts (94.6 to 946.3 $cm^3$), and most preferably equaling about 5 quarts (473 $cm^3$). However, the dimensions and volume of the wall-safe 30a can readily be customized to suit specific facility requirements.

The wall-safe 30a additionally includes a pair of baffles 52, 54 positioned to allow medical waste to fall into the holding chamber 48a when deposited through the inlet aperture 46a. Baffles 52, 54 are positioned to substantially prevent deposited medical waste from spilling out the inlet aperture 46a if the wall-safe 30 is inadvertently tipped. Each baffle 52, 54 extends inwardly from the side walls 50a of the wall-safe 30a generally at an angle of about 45°±30°, and more preferably at about 30° from the plane of the side wall 50a to form a downwardly inclined ramp.

In a preferred embodiment, the generally rectangular box configuration of the wall-safe 30a has a height of about 11.5 inches (29.2 cm), a depth of about 4.0 inches (10.2 cm), and a width of about 7.75 inches (19.7 cm). The inlet aperture 46a in the illustrated embodiment has a rectangular configuration of about 2.0 inches (5.1 cm) by about 7.5 inches (19.1 cm). The wall-safe 30a includes a first baffle 52 extending from an upper corner 56 of the wall-safe 30a and projecting downwardly towards the holding chamber 48a at an angle of about 30°. The first baffle 52 spans the length of the wall-safe 30a with a length of about 7.75 inches (29.2 cm) and projects into the holding chamber 48a with a width of about 4.0 inches (10.2 cm).

The wall-safe 30a additionally includes a second baffle 54 attached to the walls 50a of the wall-safe 30a at a position of about 3.0 inches (7.62 cm) from the top of the wall-safe 30a, opposite the first baffle 52, and extending at an angle of about 30° from the side wall 50a of the wall-safe 30a. The second baffle 54 spans the length of the wall-safe 30a with a length of about 7.75 inches (29.2 cm), and projects into the interior of the holding chamber 48a with a width of about 4.0 inches (10.2 cm). The first baffle 52 and the second baffle 54 consequently separate the holding chamber 48a from the inlet aperture 46a. The holding chamber 48a, configured accordingly, holds about 5 quarts (473 cm$^3$) of waste material.

Referring to FIG. 6, the wall-safe 30a additionally includes a pair of brackets 58a disposed on the lower edges of the rectangular box, along the edges of a selectively sealable bottom aperture 60a. The brackets 58a define a pair of parallel slots 62a which receive a slidable door 84, the side edges 86 of the door 84 sliding between the pair of parallel slots 62a. In this manner, the brackets 58a support the door 84 which closes the bottom aperture 60a.

The door 84 preferably includes a locking mechanism 68a to prevent unauthorized persons from removing the door 84 from the wall-safe 30a. The locking mechanism 68a preferably comprises a conventional lock cylinder 70a coupled to a throw lever 72a which rotates in and out of engagement with the adjacent side wall 50a of the wall-safe 30a to lock and unlock the door 84, respectively. The wall-safe 30a, proximate the locking mechanism 68a, includes an aperture (not shown) which receives the lock cylinder 70a and throw lever 72a when the door 84 is inserted between the lower brackets 58a.

The door 84 also includes a pair of cylindrical pegs 74a which extend from the bottom surface of the door 84, away from the wall-safe 30a. The pegs 74a interact with the hopper mechanism 20, as discussed in detail below.

The wall-safe 30a further includes a handle 76a to facilitate carrying the reusable wall-safe 30a between the mounting bracket (not shown) positioned in the medical facility room and the disposer unit 10 preferably located in a remote location of the medical facility.

As illustrated in FIG. 5, a disposable tray 78 is preferably positioned in the wall-safe 30a to prevent fluids, which drain from the medical waste, from spilling through spaces between door 84 and the wall-safe bottom aperture 60a. Preferably, the tray comprises cellophane or other conveniently disposable material.

The tray 78 is defined by four side walls 80 having a height of at least about 1.5 inches (3.8 cm) and a bottom 82 having a size generally coextensive with the bottom aperture 60a. The disposable tray 78 is preferably positioned on top of the bottom door 84 with the wall-safe 30a initially empty and is disposed with the medical waste when the wall-safe 30a is emptied into the disposer unit 10, as discussed below.

Hopper Mechanism

Referring to FIGS. 1 and 5, the hopper mechanism 20 includes a platform 90 mounted on a top surface 92 of the cabinet 12. The platform 90 is provided with a central aperture 94 having a shape complementary to that of the wall-safe bottom aperture 60. The platform 90 further includes a pair of parallel rails 96 running along the sides of the central aperture 94 and being configured to receive the lower brackets 58 of the wall-safe 30. The rails 96 extend from a position proximate the front side of the central aperture 94 and extend along the length of the central aperture 94. The platform 90 further includes a pair of holes 98 positioned in front of the central aperture 94 and spaced apart by an amount equal to the spacing between the pegs 74 of the wall-safe door 64.

The platform is preferably formed from an inert, durable material, such as, for example, a ultra high molecular weight polycarbonate, stainless steel or like material.

As best seen in FIG. 1, a lid 99 covers the central aperture 94 and is manually pivotable about a hinge 101 to expose the central aperture 94. The lid 99 includes a handle 103 to facilitate opening and closing the lid 99.

Figure 7A:
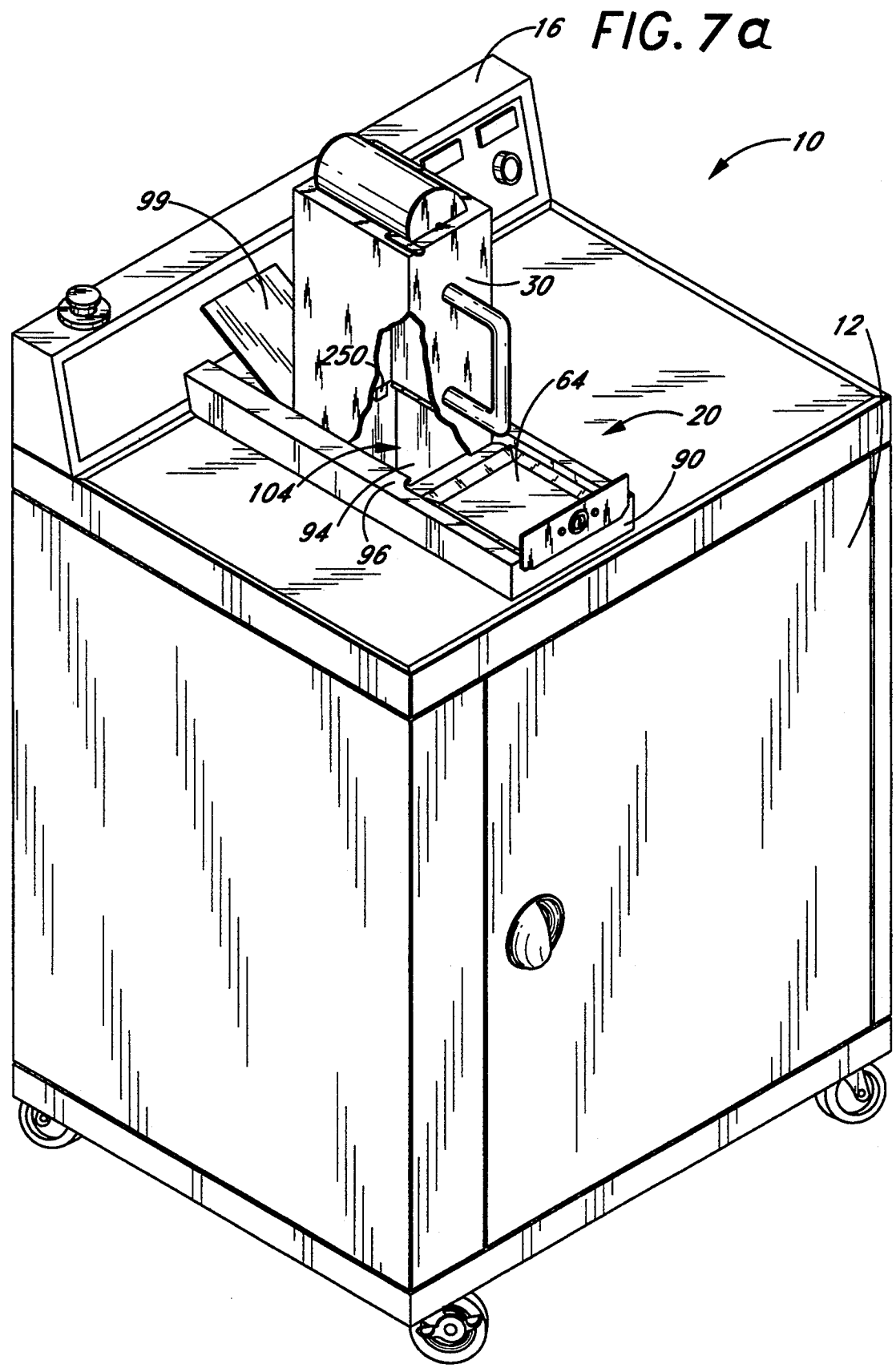
FIG. 7a is a top perspective, partial cut-away view of the waste disposal system of FIG. 1, illustrating the interaction between the wall-safe and a disposer unit.
Figure 7B:
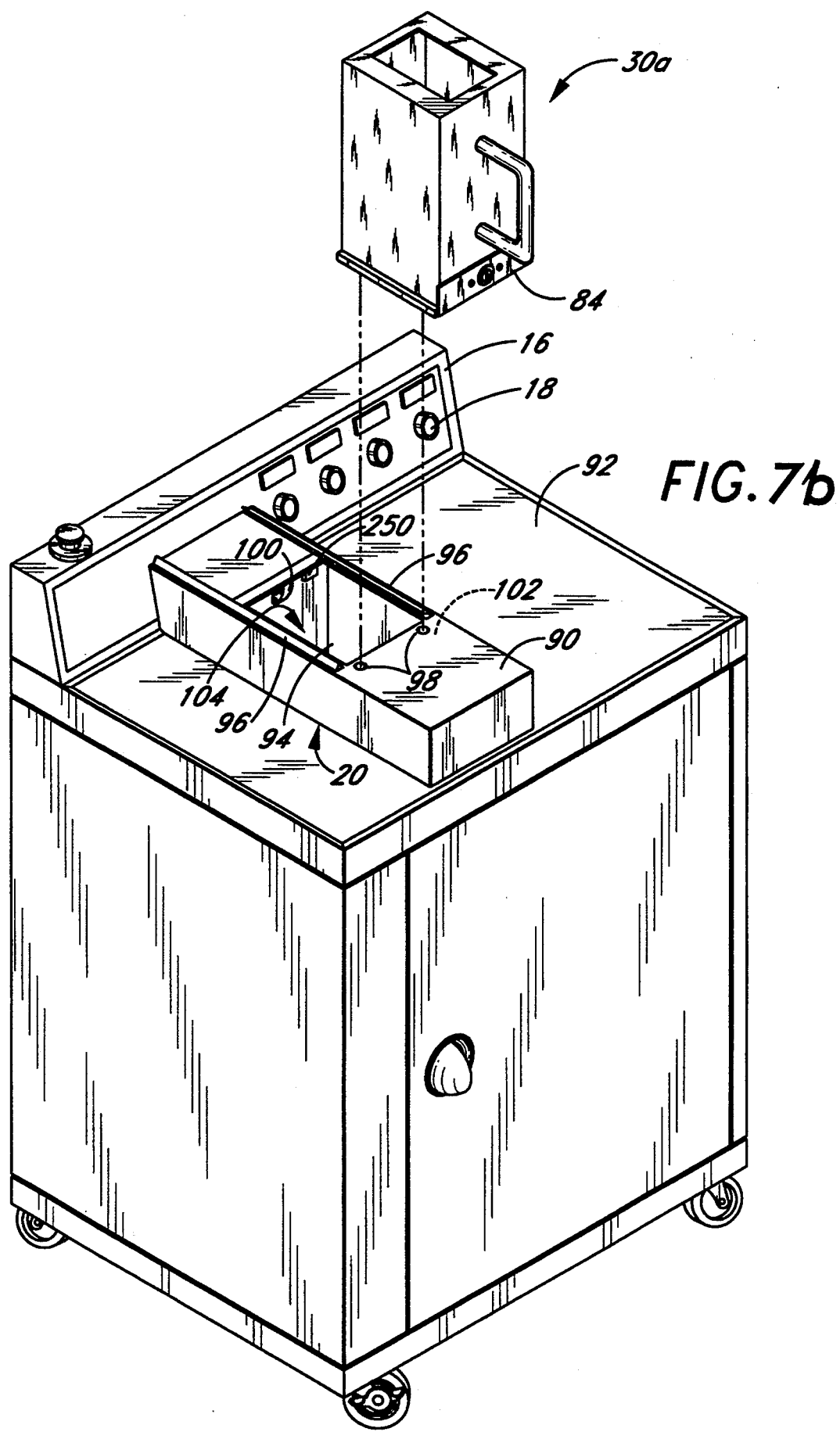
FIG. 7b is a top perspective view of another embodiment of a waste disposal unit in accordance with the present invention, illustrating an automated retractable hopper lid.

Alternatively, as illustrated in FIG. 7b, the hopper mechanism 20 includes a retractable lid 100 covering the central aperture 94 and being driven by a motor via a rack and pinion mechanism (not shown). The motor is connected to a micro-switch 102 positioned adjacent to one of the platform rails 96. The micro-switch 102 is activated by sliding the wall-safe 30 between the rails 96, as discussed in detail below. Alternatively, the lid 100 is driven by a magnetic mechanism, activated when the wall-safe 30 is placed between the platform rails 96.

Referring to FIG. 2, the central aperture 94 of the platform 90 opens into a disposer chute 104, which connects the platform aperture 94 with an inlet 106 of the disposer 22. The disposer chute 104 preferably has a rectangular cross-sectional shape corresponding to the shape of the platform aperture 94. The hopper mechanism 20 also includes the retractable gate 34 positioned between the platform aperture 94 and the disposer inlet 106. The retractable gate 34 is connected to a motor 108 via a rack and pinion mechanism 110 which slides the gate 34 from a closed position to an open position to place an upper portion 112 of the chute 104 above the gate 34 in communication with the disposer inlet 106. The motor 108 is connected to the program logic computer 28 which opens and closes the gate 34, according to the operation sequence. The hopper gate 34 prevents splash-back of the fluid in the disposer 22 when the medical waste is emptied from the wall-safe 30, as discussed in detail below.

The chute upper portion 112 preferably holds a volume of medical waste preferably equal to the volume held by the wall-safe 30, and more preferably holds a volume of about 5 quarts (473 cm$^3$) of medical waste.

The Disposer

Figure 8:
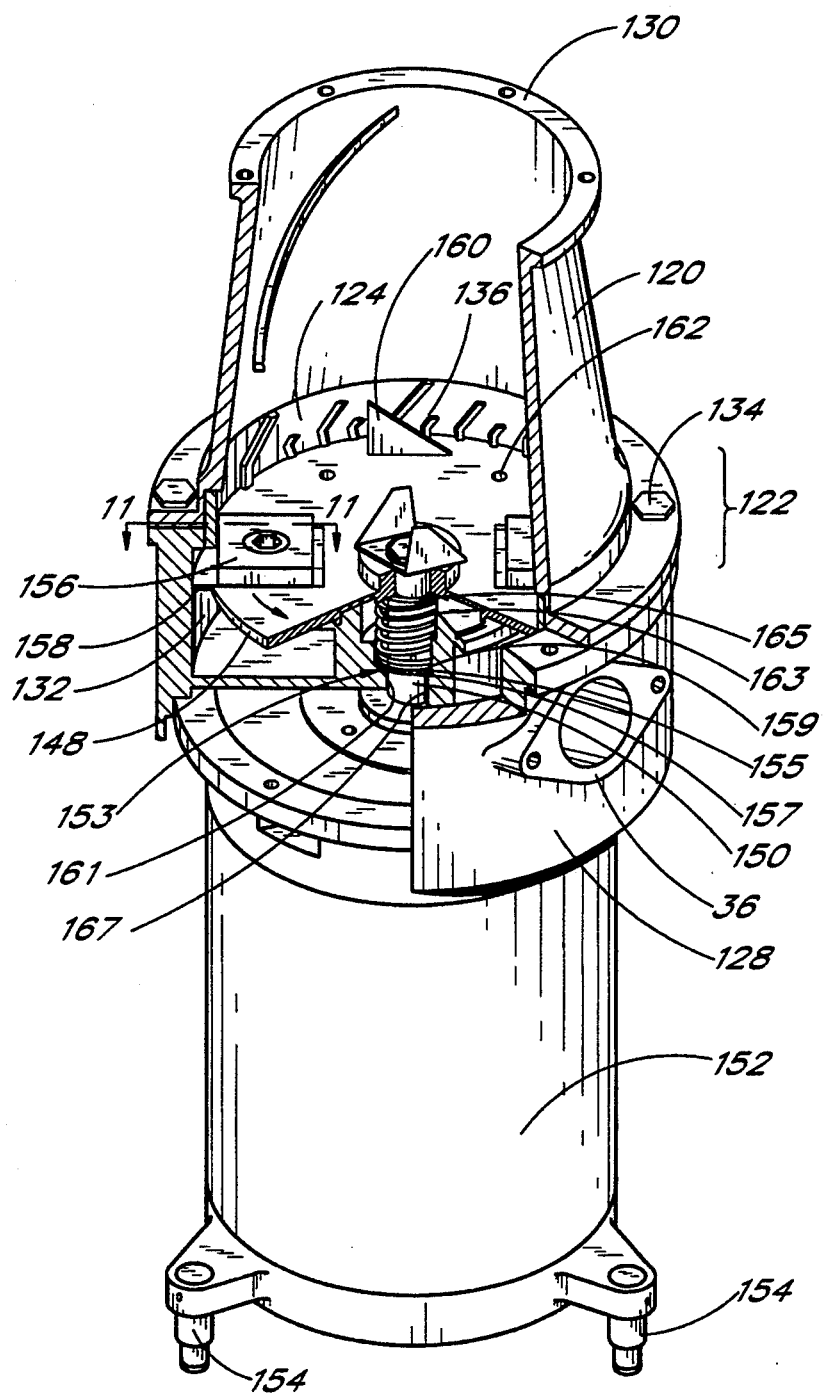
FIG. 8 is a top perspective, partial cut-away view of a disposer of the waste disposal unit of FIG. 2.
Figure 9:
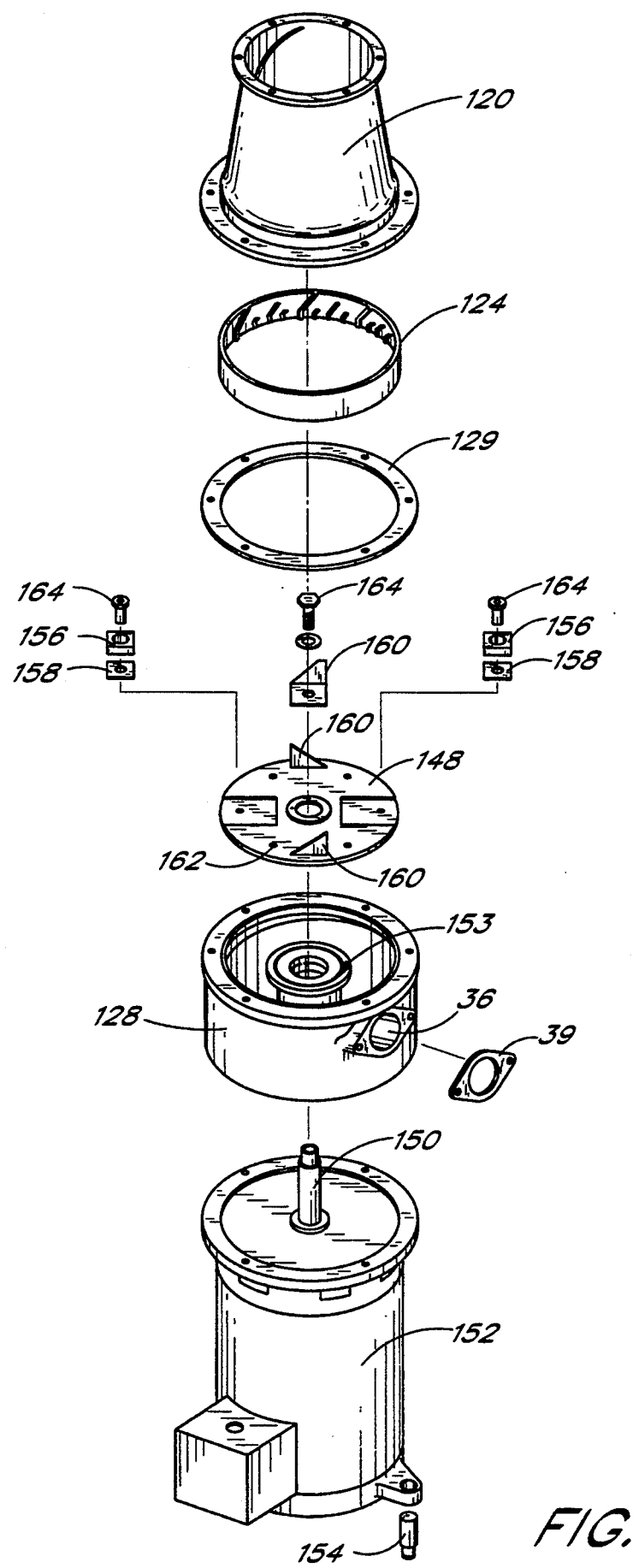
FIG. 9 is an exploded perspective view of the disposer of FIG. 8.

Referring to FIGS. 8 and 9, the disposer 22 comprises the upper grinding chamber 32 defined by an upper housing portion 120, a cutting assembly 122 including a shear ring 124 to reduce the medical waste deposited in the grinding chamber 32, and a lower discharge chamber 126 defined by a lower housing portion 128 which receives the reduced materials and directs the materials through the discharge port 36 connected to the discharge conduit 38.

The upper and lower housing portions 120, 128 form a hollow metal housing, sealed by a central gasket 129. The upper housing portion 120 is generally cylindrical shaped and supports an annular top flange 130 which circumscribes the inlet opening 106. The bottom housing portion 128 is generally cup-shaped and includes a central bottom opening 132 positioned coaxially with the cylindrical top portion 120 of the housing. As seen in FIG. 8, the top and bottom housing portions 120, 128 are connected together by a plurality of bolts 134 and cooperate internally to define an annular recess for tightly receiving and holding the shear ring 124 positioned concentrically about the central axis of the housing.

Figure 10:
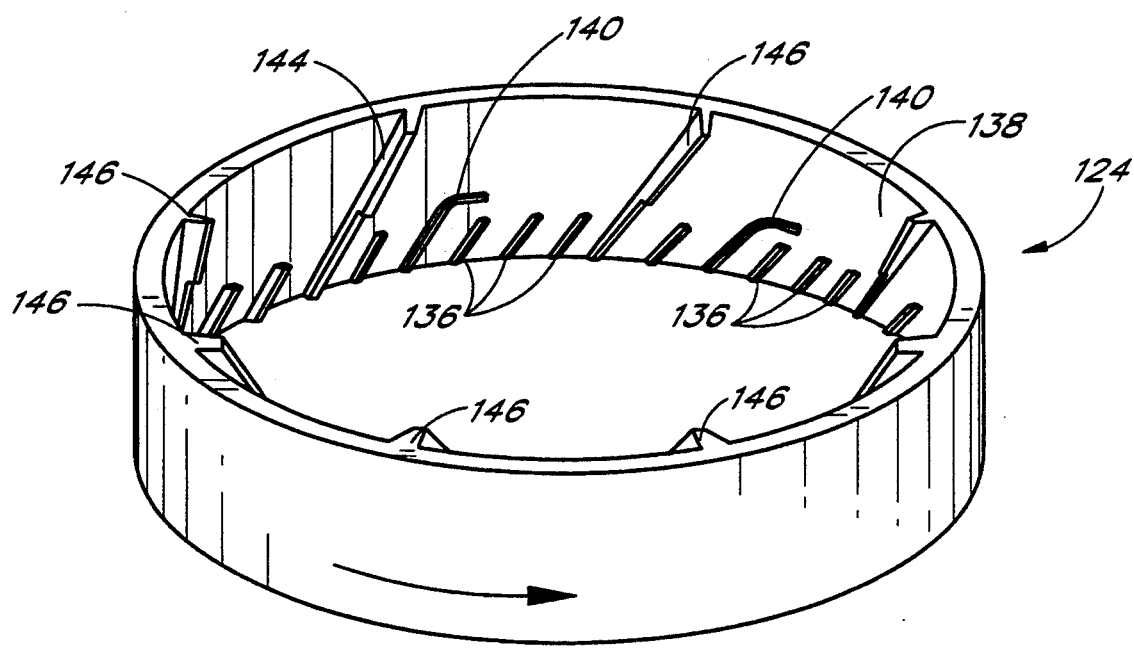
FIG. 10 is a perspective view of a shear ring of the disposer of FIG. 8.

Referring to FIGS. 8 and 10, the shear ring 124 includes a series of spaced cutting teeth 136 extending from and carried by an internal wall 138 of the shear ring 124. Each cutting tooth 136 extends at an angle from the central axis of the disposer 22, preferably by about 15° to 75°, more preferably by about 30° to 60°, and most preferably by about 45°. Each tooth 136 is also positioned in a plane parallel to the central axis, with the axis of the inner arcuate surface 138 of the shear ring 124 being collinear with the central axis. Every sixth tooth 140 of the shear ring 124 includes a top portion 142 which extends above the tops of the adjacent tooth 136 in a generally horizontal plane to form a plurality of inverted, generally L-shaped teeth 140 in a series of teeth 136. Separated from each L-shaped tooth 140 by a single tooth 136 is an elongated tooth 144 which extends the axial height of the shear ring 124 and includes an enlarged upwardly inclined top portion 146 above the tops of the other teeth 136, 140 in the series. The L-shaped teeth 140 and the enlarged teeth 144 trap and direct waste materials between the other teeth 136 of the shear ring 124 and cooperate with the balance of the cutter assembly 122 to enable the disposer 22 to rapidly and reliably reduce the medical sharps into small fragments or into unrecognizable waste, as discussed below. The illustrated form of the shear ring 124 has proven to be the optimal array of teeth 136 this purpose.

Referring to FIGS. 8 and 9, the cutter assembly 122 further includes a disk or flywheel 148 of a slightly smaller outer diameter than the inner diameter of the shear ring 124. The disk 148 is connected to an upper end of a vertical drive shaft 150 of a motor 152 to turn about the central axis of the disposer 22 within the shear ring 124. In this regard, the vertical drive shaft 150 of the motor 152 extends upwardly through the bottom opening 132 in the lower housing portion 128 along the central axis thereof and through a seal assembly 153.

The seal assembly 153 supports the drive shaft 150 and seals the lower aperture of the discharge chamber 126. The seal assembly 153 preferably comprises a fluoroelastomer (e.g., VITON®) O-ring 155 sandwiched between a bronze mating ring 157 and a seal head 159. The seal head 159 is preferably a Buna-n and Graphite ring. The seal assembly 153 is positioned inside a seal cavity 161 of the lower housing 128. With the drive shaft 150 passing through the seal assembly 151, a spring 163 is placed over the drive shaft 150 and is held between the seal head 159 and a cap 165. The spring biases the seal assembly 153 against a lower flange 167 of the seal chamber 161. The disk 148 attached to the end of the drive shaft 150 to secure the cap 165 in place.

The motor 152 preferably has a 1.5 to 10 horsepower (hp) (1120 to 7460 watts (W)) capacity, depending upon the volume of waste material desirably being processed during a single disposal cycle. The motor 152 is connected to and extends downwardly from the bottom of the lower housing portion 128 and carries a plurality of feet 154 which are anchored to the bottom of the cabinet 12.

Figure 11:
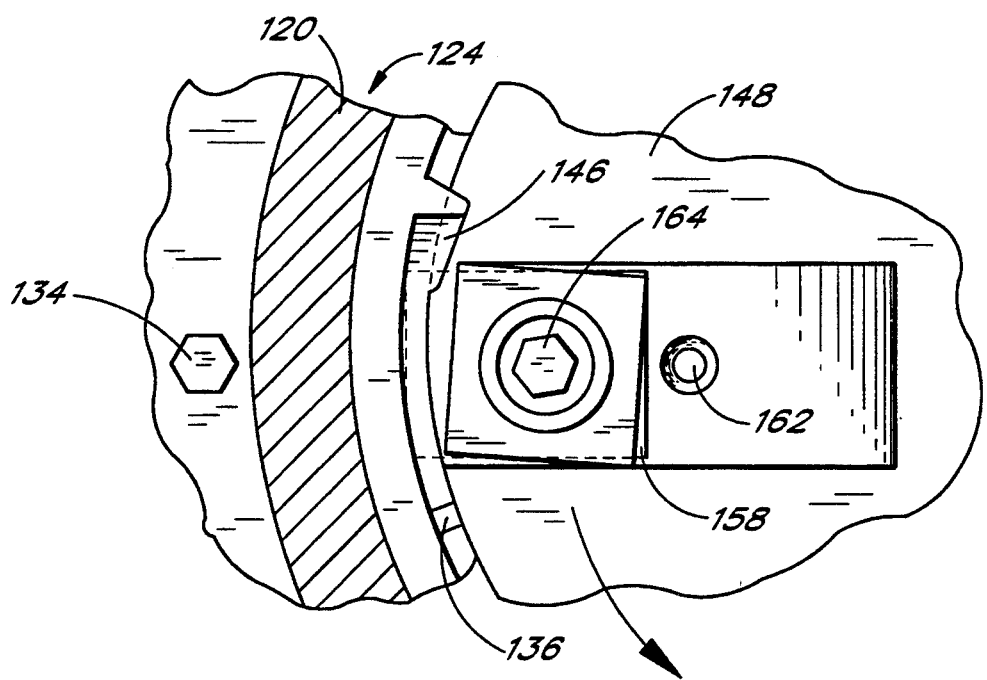
FIG. 11 is a fragmentary sectional view taken along line 11—11 of FIG. 8.

The disk 148 support is a plurality of cutting blocks 156 and associated cutting blades 158 positioned around the circumference of the disk 148 and positioned adjacent to the lower portion of the shear ring 124 in the assembly. A plurality of bolts 164 fasten the cutting blocks 156 and cutting blades 158 to the disk 148. As illustrated in FIG. 11, the cutting blocks 156 are angled slightly such that only one vertical edge of the block 156 engages the inner surfaces of the teeth 136 as the disk 148 turns.

With this arrangement of the cutter assembly 122, the medical waste deposited into the disposer 22 through the inlet opening 106 falls on the top of the disk 148. Operation of the motor 152 rapidly rotates the disk 148 in a counterclockwise direction in the illustrated form. At least one hammer 160 extends upwardly from the top of the disk 148 to strike and break up large objects as the disk 148 turns. The hammer 160 also acts with the centrifugal force developed by the disk 148 to throw the waste material rapidly outwardly against the inner wall 138 of the ring shear 124. Simultaneously, the waste material is carried by the disk 148 in a circular path against the teeth 136 of the shear ring 124.

As the waste material rotates with the disk 148, it is captured and downwardly directed between the other teeth 136 of the shear ring 124 by the L-shaped teeth 140, as well as by the enlarged teeth 144. The captured waste material is then repeatedly sheared by the vertical teeth of the cutting blocks 156 as they travel around and are in contact with the inner faces of the teeth 136. The sheared material passes downwardly below the shear ring 124 between the teeth 136 thereof. There, the material is sheared a second time by the cutter blades 156 carried by the disk 148. This double shearing action reduces even the most dense waste material and allows the material to flow with the sterilant between the outer edge of the disk 148 and the bottom of the ring 124 into the lower discharge chamber 126. From the discharge chamber 126, the slurry of waste material and sterilant flows through the discharge port 36 and through the discharge conduit 38 into the waste receptacle 26.

When the waste material has been completely reduced and disposed by the cutter assembly 122, the disposer 22 may be internally cleaned by continuing to run sterilant therethrough, with drains between the outer edges of the disk 148 and the shear ring 124 and through drain ports 162 in the disk 148. The drain ports 162 prevent sterilant from accumulating within the disposer 22 after the disposer 22 has been turned off.

In practice, the continual capturing and shearing between the cutter blocks 156, the angle teeth 136 and L-shaped teeth 140 of the cutter ring 124, as well as the shearing action between the bottoms of the teeth 136 and the cutter blades 158, has been found to rapidly reduce medical waste into either small fragments or into harmless, twisted pieces. In this respect, the illustrated array of teeth 136, inclined at 45° angles, and including space arrangements of L-shaped and enlarged teeth 140, 144 has proven to provide optimum waste reducing results.

Waste Receptacle

Figure 12:
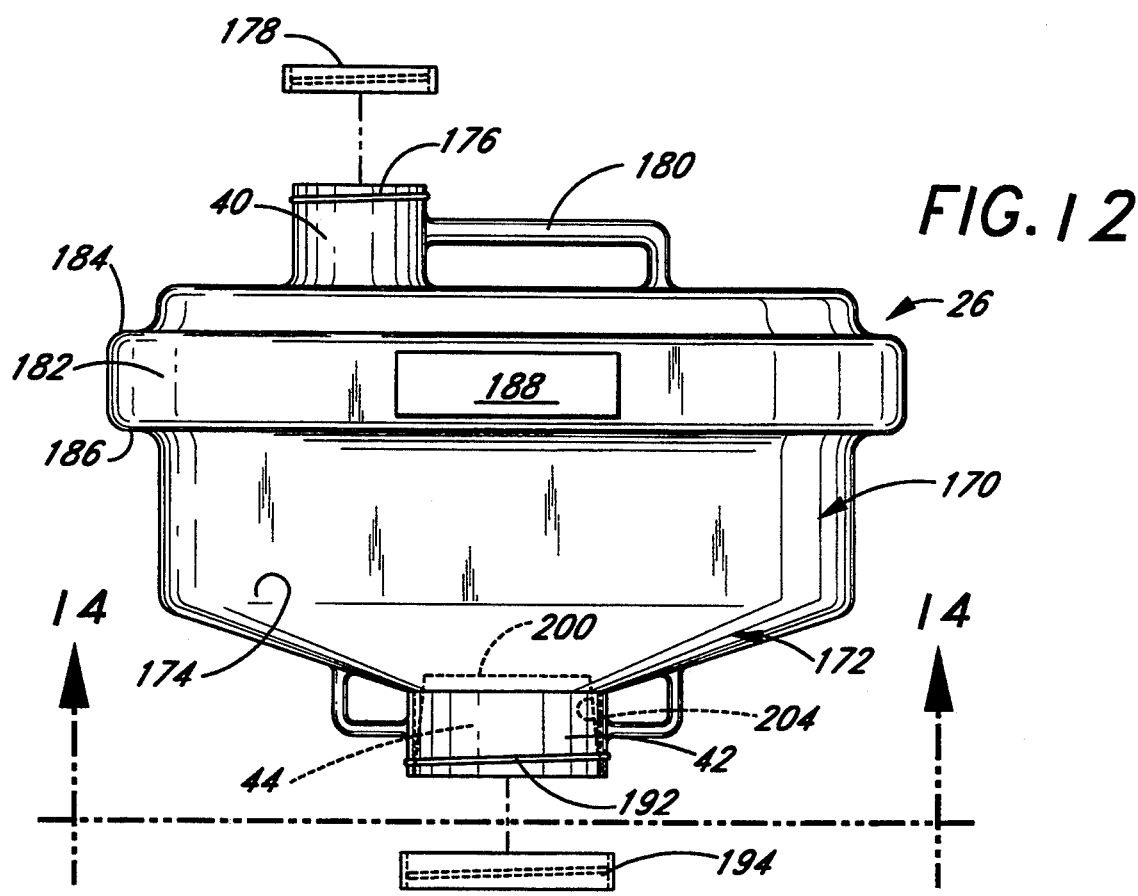
FIG. 12 is side elevational view of a disposable waste receptacle of the waste disposal system of FIG. 2.
Figure 13:
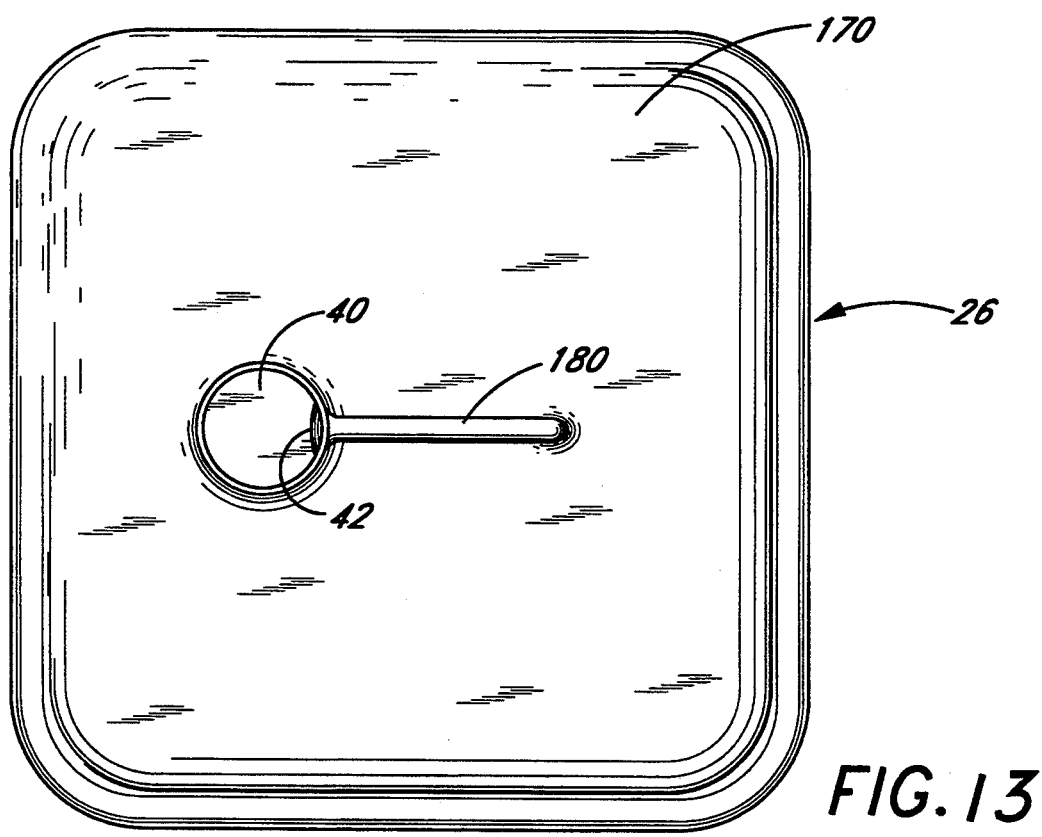
FIG. 13 is a top plan view of the waste receptacle of FIG. 12.

Referring to FIGS. 12 through 14, the disposable waste receptacle 26 has a durable, hollow plastic body formed by a generally cubic upper portion 170 and a generally funnel-liked shaped (i.e., generally inverted pyramidical shaped) lower portion 172. The lower portion 172 has a top section 174 with a generally square cross-sectional shape corresponding to the cross-sectional shape of the upper portion 170. The lower portion 172 tapers in cross section from the generally square top section to a generally circular bottom section, terminating into the effluent port 42. As best seen in FIG. 12, the lower portion 172 thus has a significantly smaller cross-sectional area proximate the effluent port 42 than it has proximate the upper portion 170 to maximize drainage through the waste receptacle 26.

The waste receptacle 26 defines an internal volume ranging between 1 and 100 quarts (94.6 and 9,463.5 cm$^3$), more preferably ranging between 10 and 50 quarts (946.3 and 4,730 cm$^3$), and most preferable ranging between 35 and 40 quarts (3,310 and 3,780 cm$^3$).

The waste receptacle 26 further includes the influent port 40 communicating with the upper portion 170 of the waste receptacle 26. The influent port 40 supports an external thread 176 configured to engage a top end cap 178 which closes the influent port. Alternatively, the top cap 178 could snap onto the influent port 40, the components 40, 178 having cooperating structure as known in the art. The waste receptacle 26 also comprises a handle 180 attached between the upper portion 170 and the influent port 40 to ease handling the waste receptacle 26.

The waste receptacle 26 includes a rib 182 having a generally rectangular shape and circumscribing the exterior of the waste receptacle body 26. The rib 182 is defined between a generally flat upper surface 184 and a generally flat lower portion 186. The rib 182 preferably includes a flat label surface 188 to facilitate labeling the waste receptacle 26.

The waste receptacle 26, at its lower end, attaches to the effluent port 42 which projects away from the body. The effluent port 42 supports an external thread 192 configured to engage a lower end cap 194 to seal the waste receptacle 26. The lower cap 194 could alternatively snap onto the effluent port, the components 42, 194 having cooperating structures as known in the art.

As best seen in FIG. 13, the longitudinal axes of the influent port 40 and the effluent port 42 are off-set from each other. That is, the axes of each port 40, 42 are parallel, but not collinear. The slurry of processed medical waste and sterilant thus strikes the side portion 196 of the receptacle 26 before flowing into the filter 44 to improve the performance of the filter 44.

The waste receptacle 26 further includes a filter 44 preferably disposed within the effluent port 42. In one embodiment, the filter 44 has a hollow frusto-conical shape having a plurality of apertures disposed over its surfaces. The frusto-conical shape increases the surface area of the filter, as compared to a filter spanning across the open end of the effluent port 42.

As illustrated in FIG. 14, the filter 44 includes a plurality of small apertures 198 extending through its upper surface 200. The filter 44 also includes a plurality of longitudinal slots 202 extending through the side wall 204 of the filter 44 and each being positioned generally within a plane that includes the longitudinal axis of the frusto-conical shape. The filter 44 also comprises a small spacing mesh (not shown) positioned over the side wall 204 of the filter 44. The mesh 204 preferably has a grid spacing of 3/16 inch (0.47 cm) on center with a hole size of 1/16 inch (0.16 cm).

As illustrated in phantom lines in FIG. 12, the filter 44 projects into the lower portion 172 of the receptacle 26 from the lower end of the effluent port 42. The filter 44 substantially prevents the ground medical waste from escaping through the effluent port 42 as the excess sterilant flows through the port 42.

Referring to FIG. 2, the waste receptacle 26 is positioned proximate to the disposer 22 and in communication with the disposer 22 via the discharge conduit 38. The waste receptacle 26 is supported within the disposer unit 10 by a pair of brackets 206 which embrace the rib 182 of the receptacle body 26. The brackets 206 are preferably mounted on a pair of vibrators 208 which support the lower planar surface 186 of the waste receptacle rib 182. The vibrators 208 vibrate the waste receptacle 26 during use to enhance sterilant flow through the waste receptacle 26 and to level the waste deposited in the waste receptacle 26.

Sterilant Recirculation System

Referring to FIG. 2, the sterilant recirculation system 24 includes a holding tank or reservoir 220 positioned below the waste receptacle 26 which receives the sterilant flowing through the effluent port 42. The holding tank 220 has a volume capacity ranging between 1 gallon and 50 gallons (378 and 18900 cm$^3$), preferably ranging between 5 and 10 gallons (1890 and 3780 cm$^3$), and most preferably equal to about 7 gallons (1890 cm$^3$). The holding tank 220 includes a quick dump drain 222 positioned at the bottom of the tank 220 and includes an incline bottom 224 tapering to the drain 222. A conventional gate valve 226 opens and closes the drain 222. The holding tank 220 further includes a pair of filters (not shown) positioned in series and disposed between the effluent port 42 and an outlet port 228 of the holding tank 220 in order to trap any ground waste which passes through the filter 44 of the waste receptacle 26.

The recirculation system 24 further includes a pump 230 in communication with the holding tank 220 via the holding tank outlet port 228. The pump 230 pumps the recovered sterilant through a return line 232 connected to the disposer grinder chamber 32 where the sterilant is sprayed into the disposer 22. The pump 230 preferably has a capacity of 960 gallons per hour (3.63 meter$^3$/hour) and is corrosion resistant. The pump 230 more preferably is a Little Giant ® model #4-MD-HC pump, commercially available from the Little Giant ® Pump Company.

The holding tank 220 also communicates with a chemical tank 234 which holds a chemical component of the sterilant. The chemical tank 234 preferably hold of about 7 to 8 gallons (approximately 0.026 m$^3$) and is filled through a stand pipe (not shown) accessible through a top cap 236 (FIG. 1) located on the panel 16 of the cabinet 12.

A pump 238 is positioned between the holding tank 220 and the chemical tank 234 to supply fresh chemical such as chlorine to the holding tank 220 either after dumping the contents of the holding tank 220 or after the concentration of chlorine in the aqueous solution drops below a preselected concentration level, as discussed in detail below. The pump 238 is preferably a low flow, corrosive resistant pump, such as the type commercially available from the Little Giant ® Company.

The holding tank 220 further selectively communicates with a pressurized water source (not shown), such as a standard water inlet line of the medical facility. A solenoid valve (not shown) connected to the water inlet line controls the flow of water into the tank 220, primarily during a refill sequence, as discussed below.

Preferably, the recommended concentration of sterilant automatically flushes waste, insuring safe and efficient sterilization during the duration of each disposal cycle. The sterilant preferably comprises a chlorine compound, and more preferably a sodium hypochlorite solution to inactivate vegetative bacteria, fungi, viruses and mycobacteria contaminating the medical waste. Sodium chlorite solutions with variable concentrations of free, available chlorine have been shown to inactivate a variety of bacterial spores. Such inactivation is dependant upon the initial concentration of free, available chlorine, the Ph, the temperature, the length of time of contact with the spores and the presence of interfering substances such as organic material. Ideally, a chemical germicide used for medical waste treatment should qualify as a high level disinfectant (i.e., relative sterilization) with the ability to kill vegetative bacteria, fungi, viruses, and mycobacteria. It should also have the ability to inactivate a minimum of 10,000 bacteria spores, and maintain sanitability over time. The sporicidal capacity of high concentrations of sodium hypochlorite (e.g., 2,750 and 5,550 parts per million (ppm) of free, available chlorine) under severe organic material challenge and dissolution has demonstrated to be effective when used in mechanical/chemical medical waste treatment systems. Thus, it is preferred that the sterilant comprise sodium hypochlorite having a concentration of free, available chlorine ranging between 2,750 and 5,550 ppm, although other concentrations and chemical systems can be readily identified through routine experimentation by one of skill in the art.

Control System

Referring to FIG. 2, the program logic computer 28 controls the operation of the disposer unit 10. The program logic computer 28 preferably comprises a programmable controller, such as the D100 micro-programmable logic controller commercially available from Cutler-Hammer and distributed through Eaton. The computer 28 is a stand-alone programmable logic controller containing a central processing unit (CPU), power supply, memory, and input/output circuitry with terminals. The controller 28 also contains RAM memory and a back-up battery. The controller 28 is preferably capable of communicating with a personal computer (not shown), such as, for example, an XT or AT compatible computer, or the like, with supporting extended industry standard architecture, in order to facilitate programming.

The program logic computer 28 is connected to a plurality of electro-mechanical mechanisms which sense and control various components of the disposer unit 10. The program logic computer 28 is connected to a micro-switch or rocker switch 250 positioned proximate the platform aperture 94, activation of which begins the disposal cycle. The micro-switch 250 is activated when the wall-safe 30 is positioned between the platform rails 96 and slid over the open platform aperture 94. The program logic computer 28 shuts off all components of the disposal unit 10 if the wall-safe is disengaged from the rocker switch 250 by sliding the wall-safe 30 from an engagement position covering the central aperture 94.

With the wall-safe 30 actuating the rocker switch 250, the program logic computer 28 communicates with a level sensor 252 to determine whether the chemical tank 234 is above an acceptable level (e.g., is generally about one-third full). The program logic computer 28 activates a display light 18 when the chemical tank 243 is below a specific level to indicate that the chemical tank 234 needs filling.

The program logic computer 28 also determines when the waste receptacle 26 is full. The program logic computer 28 keeps track of the number of disposal cycles performed between changings of the waste receptacle 26. That is, after a new waste receptacle has been inserted into the disposer unit 10, the program logic computer 28 counts the number of times that the disposer 22 has been activated in order to determine when the waste receptacle 26 is full. With a waste receptacle 26 having a holding capacity of about 35 to 40 quarts (3310 to 3780 $cm^3$), and with a disposal unit 10 being designed for processing about 5 quarts (473 $cm^3$) of waste material during a single disposal cycle, the waste receptacle 26 becomes full after about eight (8) disposal cycles. When the program logic computer 28 determines that the disposer unit 10 has gone through eight (8) disposal cycles from the last changing of the waste receptacle 26, the program logic computer 28 activates a panel light 18 to indicate that the waste receptacle 26 needs to be changed.

Moreover, the program logic computer 28 will not activate the disposer unit 10 until the waste receptacle 26 has been changed and a reset button 254 inside the disposer unit cabinet 12 has been actuated. Although FIG. 2 illustrates the reset button 254 as a push button, of a type commercially available from Allen-Bradly, it is contemplated that the reset button 254 could comprise a rocker switch or other proximity sensing mechanism mounted proximate to the waste receptacle bracket 206 to sense when the waste receptacle 26 has been replaced. After changing of the waste receptacle 26 and actuating of the reset button 254, the program logic computer 28 begins the next counting cycle by resetting to its counter to zero and counting up again.

The program logic computer 28 also controls the concentration of the chlorine in the sterilant. After removing the filled waste receptacle 26, the sterilant in the holding tank 220 is preferably dumped, as discussed in detail below. Thereafter, the program logic computer 28 automatically fills the holding tank 220 with sterilant, mixing a desired ratio of water from the supply line with the chemical agent contained in the chemical tank 234. Specifically, the program logic computer 28 energizes the solenoid valve connected between the water supply line and the holding tank 220. The solenoid valve remains open for a preselected period of time until the holding tank 220 contains the desired amount of water. The program logic computer 28, either simultaneously or in sequence, activates the pump 238 positioned between the chemical tank 234 and the holding tank 220, to pump the chlorine into the holding tank 220 in the desired ratio. Consequently, the sterilant generally has a concentration level of chlorine above the preselected concentration criteria discussed above.

Additionally, the program logic computer 28 preferably communicates with a chlorine concentration monitoring device 256, such as, for example, a chlorine specific electrode meter, commercially available from Corning ® and distributed by Fisher-Scientific. The monitor 256 preferably includes a conventional RS-232-C serial port to digitally communicate with the program logic computer 28. The monitor 256 senses the concentration of free, available chlorine ions in the aqueous solution contained in the holding tank 220. If the level of free, available chlorine falls below the preselected concentration levels discussed above, the program logic computer 28 activates the chemical pump 238 to pump a specific amount of chlorine into the holding tank 220, thereby bringing the concentration level of chlorine above the desired concentration level.

The program logic computer 28 also communicates with the motor 152 of the disposer 22 through conventional electronic circuitry to determine if the disposer 22 is free from obstructions. If the motor 252 is not functioning, the program logic computer 28 activates a display light 18 on the panel 16 of the disposer unit 22 to indicate that the disposer 22 is jammed. The program logic computer 28 will not activate the disposer unit 10 until the disposer 22 is free from obstructions and functioning properly.

Likewise, the program logic computer 28 communicates with the recirculation pump 230 to determine whether the pump 230 is functioning properly. In addition, the program logic computer 28 preferably connects to a flow meter 258 to sense whether a blockage exists in the recirculation system 24 and whether the recirculation pump 230 is adequately functioning. If the pump 230 is functioning improperly, or if the flow through the recirculation system 24 is below the desired level, the program logic computer 28 activates an indicator light 18 on the panel 16 of the disposal unit 10 and will not activate the disposer unit 10 until the problem has been corrected.

In addition to monitoring the disposal unit 10 as discussed above, the program logic computer 28 also controls the operations of the disposal unit 10. With the microswitch 250 activated, the program logic computer 28 energizes the motor 108 connected to the hopper gate 34 and thereafter energizes the disposer 22 for a preselected grinding period. Preferably the grinding period is less than 20 minutes, more preferably ranges between 0.1 and 5 minutes, and most preferably equals about 3 minutes. During the grinding cycle, the program logic computer 28 also activates the recirculation pump 230 to pump sterilant from the holding tank 220 into the grinding chamber 32 of the disposer 22. The program logic computer 28 shuts off the disposal unit 10 at the expiration of the disposal period.

Method of Use

The above described waste disposal unit 10 and wall-safe 30 are designed to be used in connection with a waste disposal management system. The waste management system comprises method of disposing infectious medical sharps while minimizing human contact with the medical waste.

The system involves placing at least one, and preferably a plurality of wall-safes 30 throughout a medical facility. Medical personnel deposit used syringes, needles, and the like sharps in the wall-safe 30 for disposal. A technician periodically collects the wall-safes 30 and delivers them to a room of the medical facility containing at least one disposal unit 10, typically the basement of a medical facility. The technician replaces filled wall-safes 30 with fresh wall-safes 30 to prevent the wall-safes 30 from completely filling, thereby maintaining a depository for the used medical sharps.

The technician engages the wall-safe 30 with the disposal unit 10 to dispose of the medical waste contained in the wall-safe 30. That is, the technician places the pegs 74 of the wall-safe 30 into the holes 98 of the hopper mechanism platform 90. Positioned accordingly, in the embodiment illustrated in FIG. 7b, the wall-safe 30 triggers the micro-switch which causes the retractable aperture lid 100 to open. Alternatively, the technician lifts the lid 99 in the embodiment illustrated in FIG. 7a to expose the central aperture 94. The technician then unlocks the bottom door 64 and slides the wall-safe 30 towards the rear of the disposal unit 10; the wall-safe door 64 remains stationary. In this manner, the technician opens the bottom aperture 60 of the wall-safe 30 contacting only the handle 76 of the wall-safe 30.

The contents, including the blotter or disposable cellophane tray 78, fall into the upper portion 112 of the disposer chute 104 with the bottom tray 64 and the retractable aperture lid 100 open. The wall-safe activates the rocker switch 250 when positioned over the open central aperture 94. In the embodiment of FIG. 7b, removal of the wall-safe 30 from the platform 90 causes the aperture door 100 to retract in order to shield the technician from the medical waste now deposited in the disposal unit 10.

The program logic computer 28 begins the disposal cycle operation with the rocker switch 250 being triggered by the wall-safe 30. The program logic computer 28 checks the following parameters, as described above: (1) whether the waste receptacle 28 is full; (2) whether the chemical tank 234 is empty; (3) whether the recirculation pump 230 is functioning properly; (4) whether the disposal 22 is free from obstructions; and (5) whether the sterilant in the holding tank 230 has a concentration of free, available chlorine above a minimum preselected concentration level. If any one of these parameters is not acceptable, the program logic computer 28 lights the appropriate indicator light(s) 18 on the cabinet panel 16 and will not operate the disposal unit 10 until all parameters are acceptable.

The program logic computer 28, having complete its precheck of the disposal unit components, energizes the hopper gate 34 to drop the medical waste contained in the upper portion 112 of the disposal chute 104 into the grinding chamber 32. The hopper gate 34 subsequently return to a position closing the grinding chamber 32 from the upper portion 112 of the disposal chute 104. The hopper gate 34 therefore prevents fluid in the grinding chamber 32 from splashing back through the central aperture 94 of the platform 90 as the medical waste is emptied from the wall-safe 30.

The program logic computer 28 subsequently energizes the disposer 22 to grind the medical waste and sharps into small bits and pieces. As the disk 148 rotates, the hammers 160 of the disk 148 shatter large items, the shear ring 124 traps waste material forcing the material against the cutting blocks 156, the cutting blocks 156 cut the waste material with the edges of the shear ring 124 shearing the material into small particles, and the cutting blades 158 slice the waste material into small fragments.

Simultaneously, the program logic computer 28 activates the recirculation pump 230 to spray sterilant from the holding tank 220 into the grinding chamber 32. The sterilant generally sterilizes the ground medical waste. The slurry of medical waste and sterilant passes through the cutting assembly 122, through the discharge chamber 128 and through the discharge port 36 into the discharge conduit 138. The medical waste deposits into the waste receptacle 26 and the excess sterilant is recovered through the effluent port 42, as described above.

The program logic computer 28 activates the vibrators 208 during the third disposal cycle to enhance sterilant flow through the waste receptacle 26. It has been determined that vibrating the waste receptacle 26 during the first few cycles is not necessary because of the small volume of waste contained in the waste receptacle 26, and vibrating small volumes of the waste tends to cause waste to escape through the filter apertures 198, 204. During the third cycle, however, the deposited waste partially blocks the filter 44 and the vibration is desired to enhance sterilant flow through the effluent port 42.

In a preferred embodiment, the waste receptacle 26 fills with processed medical waste after about eight (8) disposal cycles. The program control computer 28 lights the indicator light 18 telling the technician to replace the waste receptacle 26 before beginning the next disposal cycle. The disposal unit 10 will not work until the technician changes the waste receptacle 26.

The technician opens the front door 15 of the disposal unit cabinet 12 to change the waste receptacle 26. The technician removes the discharge conduit 38 from the influent port 40 of the waste receptacle 26 and screws the top end cap 178 onto the influent port 40. Grabbing the handle 180 of the receptacle 26, the technician slides the receptacle 26 from between brackets 206 to a position holding the effluent port 42 of the receptacle 26 over the holding tank 220. The technician screws the lower cap 194 onto the effluent port 42 to seal the waste receptacle 26. The technician subsequently disposes the waste receptacle 26 as ordinary refuse, typically by placing it in a refuse dumpster for disposal in a landfill.

Before replacing the waste receptacle 26, the technician preferably replaces the sterilant in the holding tank 220. The technician opens the gate valve 226 which places the holding tank 220 in communication with a conventional sewer or chemical reclaim drain. The sterilant in holding tank 220 drains from the holding tank 220. The technician subsequently flushes the holding tank 220 with water using a rinse sprayer 260. The technician closes the gate valve 226 after rinsing the holding tank 220. Thereafter, the technician replaces the waste receptacle 26, pushes the reset button 254 and closes the cabinet door 15. The program logic computer 28 then fills the holding tank 220 with sterilant having the desired concentration of free, available chlorine, as described above.

Advantageously, the technician does not contact the preprocessed or processed medical waste at any point of the waste management cycle. After the medical waste is deposited in the wall-safe, human hands do not touch the contaminated waste. During the destruction and decontamination process, the technician is completely shielded from the medical waste, even when initially placing the waste into the disposal unit. Moreover, the technician only contacts the waste receptacle after processing the medical waste, thus safeguarding the technician against infection from the medical waste, when operated properly.

Although this invention has been described in terms of a certain preferred embodiment, other embodiments apparent to those of ordinary skill in the art are also within the scope of the invention. Accordingly, the scope of the invention is intended to be defined only by the claims which follow.

What is claimed is:

1. A disposal apparatus for processing and sterilizing medical waste including sharps, said disposal apparatus comprising:
    a disposer for processing the medical waste into small particles, said disposer comprising a grinding chamber which receives the medical waste;
    disposable waste receptacle means for receiving said processed medical waste from said disposer through at least one influent port and for allowing excess sterilant, not adhering to the processed medical waste, to flow freely through said processed medical waste so that the processed medical waste is not immersed in said excess sterilant, said waste receptacle means comprising a containing cavity for holding said processed medical waste, said containing cavity being constructed of a fluid impermeable material which is resistant to puncture by processed sharps, said waste receptacle means further comprising an effluent port and a filter positioned between said containing cavity and said effluent port, said influent port and said effluent port being sealable to provide a closed container when removed from said disposal apparatus, wherein said waste receptacle means comprises a first cap and a second cap, said first cap being configured to fasten to said influent port and said second cap being configured to fasten to said effluent port to seal said waste receptacle means; and
    a sterilant recirculation system defining a fluidic path between said waste receptacle and said disposer grinding chamber in which said excess sterilant flows freely through said waste receptacle means and into said recirculation system.

2. A disposal apparatus for processing and sterilizing medical waste including sharps, said disposal apparatus comprising:
    a disposer for processing the medical waste into small particles, said disposer comprising a grinding chamber which receives the medical waste;
    disposable waste receptacle means for receiving said processed medical waste from said disposer through at least one influent port and for allowing excess sterilant, not adhering to the processed medical waste, to flow freely through said processed medical waste so that the processed medical waste is not immersed in said excess sterilant, said waste receptacle means comprising a containing cavity for holding said processed medical waste, said containing cavity being constructed of a fluid impermeable material which is resistant to puncture by processed sharps, said waste receptacle means further comprising an effluent port and a filter positioned between said containing cavity and said effluent port, said influent port and said effluent port being sealable to provide a closed container when removed from said disposal apparatus, wherein said waste receptacle means generally has a funnel-like shape to maximize drainage through said waste receptacle means; and
    a sterilant recirculation system defining a fluidic path between said waste receptacle and said disposer grinding chamber in which said excess sterilant flows freely through said waste receptacle means and into said recirculation system.

3. The disposal apparatus of claim 2, wherein said effluent port is positioned at the bottom of said waste receptacle.

4. The disposal apparatus of claim 2, wherein said sterilant recirculation system comprises a reservoir for holding a volume of said sterilant.

5. The disposal apparatus of claim 4, wherein said reservoir is in selective communication with a chemical supply source and with a water supply source.

6. The disposal apparatus of claim 5, further comprising a microprocessor and at least one detector for monitoring the sterilant and automatically introducing chemical from the chemical supply source into the sterilant based upon a preselected concentration criteria.

7. The disposal apparatus of claim 6, wherein said sterilant comprises water and chlorine.

8. The disposal apparatus of claim 6, wherein the preselected concentration criteria comprises an aqueous solution having within the range of from about 2000 ppm to about 8000 ppm chemical agent.

9. The disposal apparatus of claim 2 additionally comprising a microprocessor controlling the operation of the apparatus.

10. A disposal apparatus for processing and sterilizing medical waste including sharps, said disposal apparatus comprising:
   a disposer for processing the medical waste into small particles;
   a reservoir containing sterilant;
   a waste receptacle disposed apart from said reservoir, said waste receptacle comprising:
      an influent port through which said sterilant enters said receptacle;
      an effluent port through which said sterilant exits said container;
      a container that holds said small particles from said disposer, said container being constructed of a fluid impermeable material; and
      a filter positioned between said container and said effluent port; and
   a sterilant recirculation system that circulates said sterilant from said reservoir to said disposer to said influent port to said container through said filter and effluent port and back to said reservoir.

11. A disposal apparatus as in claim 10, wherein said waste receptacle vibrates upon operation of said disposal apparatus.

12. The disposal apparatus of claim 10, wherein said influent and effluent ports each have a longitudinal axis that is defined by the direction of flow of said sterilant through said port, said longitudinal axes being offset from each another.

13. The disposal apparatus of claim 10, wherein said waste receptacle is positioned over said reservoir and above a fluid level of said sterilant held by said reservoir such that said reservoir captures excess sterilant freely draining through said effluent port of said waste receptacle.

14. The disposal apparatus of claim 10, wherein said waste receptacle is puncture resistant.

15. The disposal apparatus of claim 10, wherein said effluent port is positioned at the bottom of said waste receptacle.

16. The disposal apparatus of claim 48, wherein said reservoir is positioned below said waste receptacle to capture excess sterilant draining through said effluent port.

* * * * *

UNITED STATES PATENT AND TRADEMARK OFFICE
CERTIFICATE OF CORRECTION

PATENT NO. : 5,354,000
DATED     : October 11, 1994
INVENTOR(S) : Glenn A. Wright, et. al.

It is certified that error appears in the above-indentified patent and that said Letters Patent is hereby corrected as shown below:

```
Column  5, line 44, change "(0.32"     to --(0.32cm).--
Column  6, line 42, change "("BS")"    to --("ABS")--
Column 11, line 44, change "136 this"  to --136 for this--
Column 22, line 31, change "claim 48"  to --claim 15--
```

Signed and Sealed this

First Day of August, 1995

Attest:

BRUCE LEHMAN

*Attesting Officer*     *Commissioner of Patents and Trademarks*